United States Patent
Kase et al.

(10) Patent No.: US 12,037,332 B2
(45) Date of Patent: Jul. 16, 2024

(54) COMPOUND INCLUDING BENZIMIDAZOLE RING STRUCTURE AND ORGANIC ELECTROLUMINESCENT ELEMENT

(71) Applicant: HODOGAYA CHEMICAL CO., LTD., Tokyo (JP)

(72) Inventors: Kouki Kase, Tokyo (JP); Su-Jin Lee, Tokyo (JP); Si-In Kim, Tokyo (JP); Kazuyuki Suruga, Tokyo (JP); Yuta Hirayama, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 923 days.

(21) Appl. No.: 16/981,302

(22) PCT Filed: Mar. 20, 2019

(86) PCT No.: PCT/JP2019/011640
§ 371 (c)(1),
(2) Date: Sep. 16, 2020

(87) PCT Pub. No.: WO2019/181997
PCT Pub. Date: Sep. 26, 2019

(65) Prior Publication Data
US 2021/0009584 A1 Jan. 14, 2021

(30) Foreign Application Priority Data
Mar. 23, 2018 (JP) .................. 2018-055656

(51) Int. Cl.
*H01L 51/50* (2006.01)
*C07D 471/04* (2006.01)
(Continued)

(52) U.S. Cl.
CPC ....... *C07D 471/04* (2013.01); *H10K 85/6572* (2023.02); *H10K 50/16* (2023.02); *H10K 50/171* (2023.02)

(58) Field of Classification Search
None
See application file for complete search history.

(56) References Cited

U.S. PATENT DOCUMENTS 5,639,914 A    6/1997   Tomiyama et al.
5,707,747 A    1/1998   Tomiyama et al.
(Continued)

FOREIGN PATENT DOCUMENTS

DE    282844 A5      9/1990
JP    H08048656 A    2/1996
(Continued)

OTHER PUBLICATIONS

Kong et. al., Lewis-acid Promoted Chemoselective Condensation of 2-Aminobenzimidazoles or 3-Aminoindazoles with 3-Ethoxycyclobutanones to Construct Fused Nitrogen heterocycles; 2018; Adv. Synth. Catal. 2018, 360, 1943-1948 (Year: 2018).*
(Continued)

*Primary Examiner* — Gregory D Clark
(74) *Attorney, Agent, or Firm* — Birch, Stewart, Kolasch & Birch, LLP

(57) ABSTRACT

A compound including a benzimidazole ring structure, represented by general formula (1).
(Continued)

← 8 Cathode
← 7 Electron injection layer
← 6 Hole blocking/electron transport layer
← 5 Light emitting layer
← 4 Hole transport layer
← 3 Hole injection layer
← 2 Transparent anode
← 1 Glass substrate

[Chem. 28]

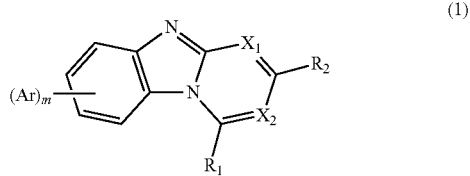

(1)

(In formula (1), $X_1$ and $X_2$ may be the same or different and each represent a specific carbon atom or a nitrogen atom, Ar represents a specific group, $R_1$ and $R_2$ may be the same or different and each represent a specific group, and m is an integer of 0-4.)

10 Claims, 1 Drawing Sheet

(51) Int. Cl.
    *H10K 85/60*    (2023.01)
    *H10K 50/16*    (2023.01)
    *H10K 50/17*    (2023.01)

(56) References Cited

U.S. PATENT DOCUMENTS

| | | | |
|---|---|---|---|
| 5,792,557 | A | 8/1998 | Nakaya et al. |
| 5,834,130 | A | 11/1998 | Kido |
| 5,869,199 | A | 2/1999 | Kido |
| 2014/0077175 | A1 | 3/2014 | Jung et al. |
| 2014/0374721 | A1 | 12/2014 | Yokoyama et al. |
| 2016/0248022 | A1* | 8/2016 | Lee ...................... H10K 85/654 |
| 2020/0231534 | A1 | 7/2020 | Yamamoto et al. |

FOREIGN PATENT DOCUMENTS

| | | | | |
|---|---|---|---|---|
| JP | 2734341 | B2 | 3/1998 | |
| JP | 3194657 | B2 | 7/2001 | |
| JP | 2004-18633 | A * | 1/2004 | ............. C09K 11/06 |
| KR | 1020150027660 | A | 3/2015 | |
| KR | 10-2015-0064442 | A | 6/2015 | |
| KR | 1020150080966 | A | 7/2015 | |
| KR | 1020190033218 | A | 3/2019 | |
| TW | 201418226 | A | 5/2014 | |
| WO | WO-2010074422 | A1 | 7/2010 | |
| WO | WO-2013054764 | A1 | 4/2013 | |
| WO | WO-2014009310 | A1 | 1/2014 | |
| WO | WO2014/043243 | A2 | 3/2014 | |
| WO | WO-2015083948 | A1 | 6/2015 | |
| WO | WO-2017111439 | A1 | 6/2017 | |
| WO | WO-2018047899 | A1 | 3/2018 | |

OTHER PUBLICATIONS

Song et. al; Cu-Catalyzed Synthesis of 3-Formyl Imidazo[1,2-a]pyridines and Imidazo[1,2-a]pyrimidines by Employing Ethyl Tertiary Amines as Carbon Sources; Org. Lett. 2017, 19, 4726-4729 (Year: 2017).*
Endo et al., "Efficient up-conversion of triplet excitons into a singlet state and its application for organic light emitting diodes". Applied Physics Letters 98, 2011, pp. 083302-1-083302-3.
Hosokawa et al., "Development of styryl-based luminescent materials", Japan Society of Applied Physics, 9th Class, Proceedings, 2001, pp. 55 to 61.
International Search Report issued Jun. 11, 2019 in PCT/JP2019/011640 (with English translation), 4 pages.
Karmakar et al., "Iridium-Catalysed Cascade Synthesis of Oxindoles Using Diazo Compounds: A Quick Entry to C-7-Functionalized Oxindoles", EurJOC., 19, 2017, 2780-2788.
Kido. "White light emitting organic EL element", Japan Society of Applied Physics, Organic Molecule and Bioelectronics Subcommittee Journal, vol. 11, No. 1, 2000, pp. 13 to 19.
Liubchak et al., "Synthesis of annulated benzimidazoles via amidine cyclization", Tetrahedron, vol. 68, No. 14, 2012, 2993-3000.
Wakimoto, "Optimization of driving lifetime durability in organic LED devices using phosphorescent guest emitter", Japan Society of Applied Physics, 9th Class, Proceedings, 2001, pp. 23 to 31.
Watanabe et al., "Organic LEDs using Hexaphenylbenzene Derivatives", 50th Applied Physics Related Union Lecture, 28p-A-6 Class, Proceedings, 2003, p. 1413.
Written Opinion issued Jun. 11, 2019 in PCT/JP2019/011640 (with English translation), 12 pages.
Taiwanese Office Action and Search Report for Taiwanese Application No. 108109710, dated Jan. 9, 2023, with English translation.
Chinese Office Action for Chinese Application No. 201980021053.2, dated Feb. 22, 2023, with an English translation.
Japanese Office Action for Japanese Application No. 2020-507865, dated Mar. 7, 2023, with an English translation.
European Office Action for European Application No. 19770662.5, dated Dec. 19, 2022.
Taiwanese Office Action for Taiwanese Application No. 108109710, dated May 23, 2023.
Baeza, Alejandro et al: "Heterocyclizations with Tosylmethyl Isocyanide Derivatives. A New Approach to Substituted Azolopyrimidines", The Journal of Organic Chemistry, vol. 70, No. 12, Jun. 1, 2005, URL: https://pubs.acs.org/doi/pdf/10.1021/jo050029r>, XP055854757, pp. 4879-4882.
Chu, Jean-Ho et al: "Substituent Electronic Effects Govern Direct Intramolecular C—N Cyclization of N-(Biphenyl) pyridin-2-amines Induced by Hypervalent Iodine(III) Reagents", The Journal of Organic Chemistry, vol. 79, No. 23, Nov. 18, 2014, URL:https://pubs.acs.org/doi/pdf/10.1021/jo501822m>, pp. 11395-11408.
Extended European Search Report issued Nov. 5, 2021 in Patent Application No. 19770662.5, 9 pages.
Guangyin, Qian et al: "Hypervalent Iodine(III) Promoted Direct Synthesis of Imidazo[1,2-a]pyrimidines: Iodine (III)-Promoted Synthesis of Imidazo[1,2-a]pyrimidines", European Journal of Organic Chemistry, vol. 2014, No. 22, Aug. 1, 2014, XP055432217, pp. 4837-4843.
Rao Changqing et al: "Cu-Catalyzed Synthesis of 3-Formyl Imidazo[1,2-a]pyridines and Imidazo[1,2-a]pyrimidines by Employing Ethyl Tertiary Amines as Carbon Sources", Organic Letters, vol. 19, No. 18, Sep. 15, 2017, URL: https://pubs.acs.org/doi/pdf/10.1021/acs.orglett.7b02, XP055854749, pp. 4726-4729.
Tardy, Sebastien et al: "Synthesis and biological evaluation of benzo[4,5]imidazo[1,2-c]pyrimidine and benzo[4,5]imidazo [1,2-a]pyrazine derivatives as anaplastic lymphoma kinase inhibitors", Bioorganic & Medicinal Chemistry, Elsevier, Amsterdam, NL, vol. 22, No. 4, Jan. 10, 2014, pp. 1303-1312.
Wang, Manman et al: "Iodine/Copper(I)-Catalyzed Direct Annulation of N-Benzimidazolyl Amidines with Aldehydes for the Synthesis of Ortho-Fused 1,3,5-Triazines" Advanced Synthesis and Catalysis, vol. 360, No. 1, URL: https://api.wiley.com/onlinelibrary/tdm/v1/articles/10.1002%2Fadsc.201701126>, XP055854909, Nov. 15, 2017, pp. 86-92.
Combined Chinese Office Action and Search Report issued Aug. 31, 2022 in Chinese Patent Application No. 201980021053.2 (with English translation), 24 pages.
Chinese Office Action for Chinese Application No. 201980021053.2, dated Jul. 12, 2023, with an English translation.
Japanese Office Action for Japanese Application No. 2020-507865, dated Aug. 1, 2023, with an English translation.
Korean Office Action dated Oct. 31, 2023 for Application No. 10-2020-7026774.

* cited by examiner

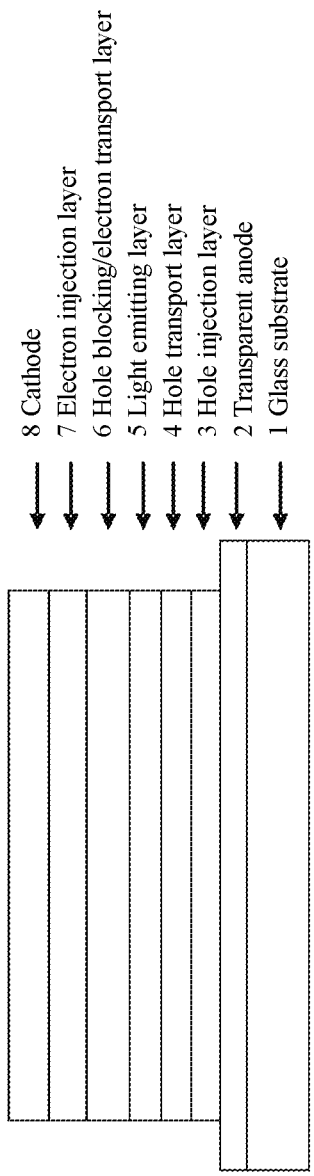

COMPOUND INCLUDING BENZIMIDAZOLE RING STRUCTURE AND ORGANIC ELECTROLUMINESCENT ELEMENT

TECHNICAL FIELD

The present invention relates to a compound suitable for an organic electroluminescence device (hereinafter abbreviated as an organic EL device) which is a light emitting device suitable for various display devices, and the device, and specifically relates to a compound having a benzimidazole ring structure and an organic EL device using the compound.

BACKGROUND ART

Since organic EL devices are self-luminescent devices, they are bright and excellent in visibility as compared with liquid-crystalline devices, and capable of giving clear display. Therefore, the organic EL devices have been actively studied.

In 1987, C. W. Tang et al. of Eastman Kodak Company put an organic EL device using organic materials into practical use by developing a device having a multilayered structure in which various roles are assigned to respective materials. They formed a lamination of a fluorescent material capable of transporting electrons and an organic material capable of transporting holes, so that both charges are injected into the layer of the fluorescent material to emit light, thereby achieving a high luminance of 1,000 cd/m$^2$ or higher at a voltage of 10 V or lower (see, e.g., Patent Literatures 1 and 2).

To date, many improvements have been performed for practical utilization of the organic EL devices. High efficiency and durability have been achieved by an electroluminescent device in which an anode, a hole injection layer, a hole transport layer, a light emitting layer, an electron transport layer, an electron injection layer, and a cathode are sequentially provided on a substrate to further subdivide various roles of the multilayered structure (see, e.g., Non-Patent Literature 1).

Moreover, for the purpose of further improvements of luminous efficiency, utilization of triplet excitation has been attempted and utilization of a phosphorescent compound has been investigated (see, e.g., Non-Patent Literature 2).

A device that utilizes light emission by thermally activated delayed fluorescence (TADF) has also been developed. In 2011, Adachi et al. of Kyushu University achieved an external quantum efficiency of 5.3% by a device using a thermally activated delayed fluorescence material (see, e.g., Non-Patent Literature 3).

The light emitting layer can be also prepared by doping a charge transporting compound, generally called a host material, with a fluorescent compound, a phosphorescent compound, or a material emitting delayed fluorescence. The choice of the organic materials in organic EL devices remarkably affects various characteristics such as efficiency and durability of the devices as described in the above-mentioned Non-Patent Literature (see, e.g., Non-Patent Literature 2).

In the organic EL device, charges injected from both electrodes are recombined in the light emitting layer to obtain light emission, and it is important how to efficiently transfer both holes and electrons to the light emitting layer. High efficiency luminescence can be obtained by enhancing electron injection property, enhancing electron mobility, enhancing a hole-blocking property of blocking a hole injected from an anode, increasing the probability of recombination of holes and electrons, and confining the excitations generated in the light emitting layer. Therefore, the roles of the electron transport material are important, and there is a demand for an electron transport material which has a high electron injection property, high electron mobility, a high hole-blocking property, and high durability for holes.

The heat resistance and amorphous property of the material are also important in terms of the lifetime of the device. In the case of a material having low heat resistance, thermal decomposition occurs even at a low temperature due to heat generated during driving of the device, and the material is deteriorated. In the case of a material having a low amorphous property, crystallization of a thin film occurs even in a short period, and the device is deteriorated. Therefore, the material used is required to have high heat resistance and good amorphous properties.

Tris(8-hydroxyquinoline) aluminum (hereinafter abbreviated as Alq$_3$), which is a typical light emitting material, is generally used as an electron transport material. However, this compound shows slow electron transfer and a work function of 5.6 eV, so that it cannot be said that the hole-blocking property is sufficient.

Compounds having a benzotriazole structure have been proposed as compounds having improved characteristics such as electron injection property and mobility (e.g., Patent Literature 3). However, in the case of a device in which these compounds are used for an electron transport layer, improvements in luminous efficiency and the like have been achieved, but it is not yet sufficient, and further lower drive voltage and further higher luminous efficiency are required.

In addition, 3-(4-biphenylyl)-4-phenyl-5-(4-t-butyl phenyl)-1,2,4-triazole (hereinafter abbreviated as TAZ) has been proposed as an electron transport material having an excellent hole-blocking property (see, e.g., Patent Literature 4).

Since TAZ has a large work function of 6.6 eV and a high hole blocking ability, TAZ is used as an electron transport hole blocking layer laminated on a cathode side of a fluorescent light emitting layer or a phosphorescent light emitting layer produced by vacuum deposition, coating or the like, and contributes to increasing efficiency of the organic EL device (see, e.g., Non-Patent Literature 4).

However, a low electron transport property is a large problem in TAZ, and it is necessary to produce an organic EL device in combination with an electron transport material having a higher electron transport property (see, e.g., Non-Patent Literature 5).

In addition, bathocuproine (hereinafter abbreviated as BCP) has a work function as large as 6.7 eV and a high hole blocking ability. However, since this compound has a glass transition point (Tg) as low as 83° C., so that a thin film thereof has poor stability, it cannot be said that the thin film functions sufficiently as a hole blocking layer.

These materials have insufficient film stability or an insufficient function of blocking holes. In order to improve device characteristics of the organic EL device, there is a demand for an organic compound having excellent electron injection and transport performance and hole blocking ability and high stability in a thin film state.

CITATION LIST

Patent Literature

Patent Literature 1: JP-A-H08-048656
Patent Literature 2: Japanese Patent No. 3194657

Patent Literature 3: WO 2013/054764

Patent Literature 4: Japanese Patent No. 2734341

Patent Literature 5: WO 2014/009310

Patent Literature 6: WO 2010/074422

Patent Literature 7: WO 2017/111439

Non-Patent Literature

Non-Patent Literature 1: Japan Society of Applied Physics, 9th Class, Proceedings, Pages 55 to 61 (2001)

Non-Patent Literature 2: Japan Society of Applied Physics, 9th Class, Proceedings, Pages 23 to 31 (2001)

Non-Patent Literature 3: Appl. Phys. Let., 98, 083302 (2011)

Non-Patent Literature 4:50th Applied Physics Related Union Lecture, 28p-A-6 Class, Proceedings, Page 1413 (2003)

Non-Patent Literature 5: Japan Society of Applied Physics, Organic Molecule and Bioelectronics Subcommittee Journal, Vol. 11, No. 1, Pages 13 to 19 (2000)

Non-Patent Literature 6: EurJOC., 19, 2780 (2017)

Non-Patent Literature 7: Tetrahedron, 14, 2993 (2012)

SUMMARY OF INVENTION

Technical Problem

An object of the present invention is to provide an organic compound having excellent characteristics of excellent electron injection and transport performance, a hole blocking ability, and high stability in a thin film state, as a material for an organic EL device having high efficiency and high durability, and to provide an organic EL device having high efficiency and high durability by using the compound.

Physical characteristics that the organic compound to be provided by the present invention should possess can include: (1) good electron injection characteristics; (2) large electron mobility; (3) an excellent hole blocking ability; (4) a stable thin film state; and (5) excellent heat resistance. The physical characteristics that the organic EL device to be provided by the present invention should possess can include: (1) high luminous efficiency and power efficiency; (2) a low light-emission start voltage; (3) a low practical drive voltage; and (4) a long lifetime.

Solution to Problem

Therefore, in order to achieve the above-described object, the present inventors focused on the fact that a nitrogen atom of a benzimidazole ring, which has electron affinity, has an ability to coordinate with a metal and excellent heat resistance. They designed and chemically synthesized a compound having a benzimidazole ring structure, and produced various organic EL devices by using the compound. As a result of intensive evaluation of characteristics of the produced devices, they completed the present invention.

The compound of the present invention capable of solving the above-described problem is represented by the following general formula (1).

[Chem. 1]

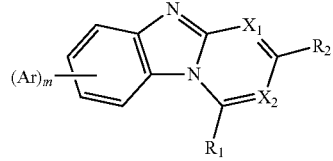

(1)

(In the formula, $X_1$ and $X_2$ may be the same as or different from each other, and each represent a carbon atom having a hydrogen atom, a deuterium atom, a fluorine atom, a chlorine atom, a cyano group, a nitro group, a trimethylsilyl group, or a triphenylsilyl group, a carbon atom having a substituted or unsubstituted aromatic hydrocarbon group, a carbon atom having a substituted or unsubstituted aromatic heterocyclic group, a carbon atom having a substituted or unsubstituted condensed polycyclic aromatic group, a carbon atom having a linear or branched alkyl group having a carbon number of 1 to 6 which may have a substituent, a carbon atom having a cycloalkyl group having a carbon number of 5 to 10 which may have a substituent, a carbon atom having a linear or branched alkenyl group having a carbon number of 2 to 6 which may have a substituent, a carbon atom having a linear or branched alkyloxy group having a carbon number of 1 to 6 which may have a substituent, a carbon atom having a cycloalkyloxy group having a carbon number of 5 to 10 which may have a substituent, or a nitrogen atom;

Ar represents a substituted or unsubstituted aromatic hydrocarbon group, a substituted or unsubstituted aromatic heterocyclic group, or a substituted or unsubstituted condensed polycyclic aromatic group;

$R_1$ and $R_2$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m represents an integer of 0 to 4.

In the case where m is an integer of 2 or more, a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring.)

In addition, the organic electroluminescent device of the present invention capable of solving the above-described problem is an organic electroluminescence device having a pair of electrodes and at least one organic layer sandwiched therebetween, and the at least one organic layer contains the compound represented by the general formula (1).

Advantageous Effects of Invention

Since a specific compound having a benzimidazole ring structure capable of effectively playing the role of injecting and transporting electrons is selected, the organic EL device of the present invention can efficiently inject and transport electrons from the electron transport layer to the light emitting layer. Therefore, an organic EL device excellent in electron injection and transport performance and the stability and durability of a thin film and having high efficiency, a low drive voltage and a long lifetime, can be achieved. The compound of the present invention can improve luminous efficiency, a drive voltage and durability of a conventional organic EL device.

BRIEF DESCRIPTION OF DRAWINGS

FIG. 1 is a diagram illustrating an organic EL device configuration of Examples 8 to 12 and Comparative Examples 1 to 3.

DESCRIPTION OF EMBODIMENTS

An embodiment of the present invention will be described in detail below. First, aspects of the present embodiment will be listed and described.

[1]

A compound having a benzimidazole ring structure represented by the following general formula (1).

[Chem. 2]

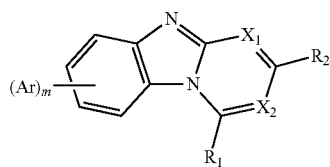

(1)

(In the formula, $X_1$ and $X_2$ may be the same as or different from each other, and each represent a carbon atom having a hydrogen atom, a deuterium atom, a fluorine atom, a chlorine atom, a cyano group, a nitro group, a trimethylsilyl group, or a triphenylsilyl group, a carbon atom having a substituted or unsubstituted aromatic hydrocarbon group, a carbon atom having a substituted or unsubstituted aromatic heterocyclic group, a carbon atom having a substituted or unsubstituted condensed polycyclic aromatic group, a carbon atom having a linear or branched alkyl group having a carbon number of 1 to 6 which may have a substituent, a carbon atom having a cycloalkyl group having a carbon number of 5 to 10 which may have a substituent, a carbon atom having a linear or branched alkenyl group having a carbon number of 2 to 6 which may have a substituent, a carbon atom having a linear or branched alkyloxy group having a carbon number of 1 to 6 which may have a substituent, a carbon atom having a cycloalkyloxy group having a carbon number of 5 to 10 which may have a substituent, or a nitrogen atom;

Ar represents a substituted or unsubstituted aromatic hydrocarbon group, a substituted or unsubstituted aromatic heterocyclic group, or a substituted or unsubstituted condensed polycyclic aromatic group;

$R_1$ and $R_2$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m represents an integer of 0 to 4.

In the case where m is an integer of 2 or more, a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring.)

[2]

The compound having a benzimidazole ring structure according to [1], represented by the following general formula (2).

[Chem. 3]

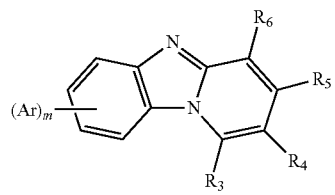

(2)

(In the formula, Ar represents a substituted or unsubstituted aromatic hydrocarbon group, a substituted or unsubstituted aromatic heterocyclic group, or a substituted or unsubstituted condensed polycyclic aromatic group;

$R_3$ to $R_6$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m represents an integer of 0 to 4.

In the case where m is an integer of 2 or more, a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring.)

[3]

The compound having a benzimidazole ring structure according to [1], represented by the following general formula (3).

[Chem. 4]

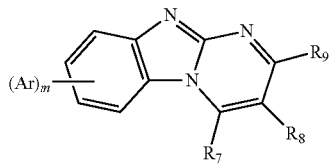

(3)

(In the formula, Ar represents a substituted or unsubstituted aromatic hydrocarbon group, a substituted or unsubstituted aromatic heterocyclic group, or a substituted or unsubstituted condensed polycyclic aromatic group;

$R_7$ to $R_9$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m represents an integer of 0 to 4.

In the case where m is an integer of 2 or more, a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring.)

[4]

The compound having a benzimidazole ring structure according to [1], represented by the following general formula (4).

[Chem. 5]

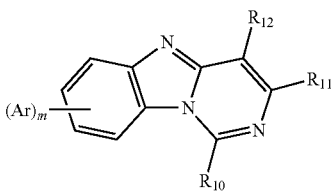

(4)

(In the formula, Ar represents a substituted or unsubstituted aromatic hydrocarbon group, a substituted or unsubstituted aromatic heterocyclic group, or a substituted or unsubstituted condensed polycyclic aromatic group;

$R_{10}$ to $R_{12}$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m represents an integer of 0 to 4.

In the case where m is an integer of 2 or more, a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring.)

[5]

The compound having a benzimidazole ring structure according to [1], represented by the following general formula (5).

[Chem. 6]

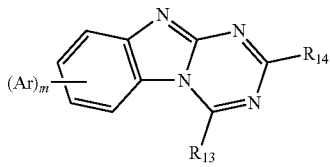

(5)

(In the formula, Ar represents a substituted or unsubstituted aromatic hydrocarbon group, a substituted or unsubstituted aromatic heterocyclic group, or a substituted or unsubstituted condensed polycyclic aromatic group;

$R_{13}$ and $R_{14}$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m represents an integer of 0 to 4.

In the case where m is an integer of 2 or more, a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring.)

[6]

The compound having a benzimidazole ring structure according to any one of [1] to [5], in which m is an integer of 1 or 2.

[7]

The compound having a benzimidazole ring structure according to any one of [1] to [5], in which m is an integer of 1.

[8]

The compound having a benzimidazole ring structure according to any one of [1] to [5], in which m is an integer of 2.

[9]

An organic electroluminescence device having a pair of electrodes and at least one organic layer sandwiched therebetween, in which the at least one organic layer contains the compound having a benzimidazole ring structure according to any one of [1] to [5].

[10]

The organic electroluminescence device according to [9], in which the organic layer containing the compound having a benzimidazole ring structure is an electron transport layer.

[11]

The organic electroluminescence device according to [9], in which the organic layer containing the compound having a benzimidazole ring structure is a hole blocking layer.

[12]

The organic electroluminescence device according to [9], in which the organic layer containing the compound having a benzimidazole ring structure is a light emitting layer.

[13]

The organic electroluminescence device according to [9], in which the organic layer containing the compound having a benzimidazole ring structure is an electron injection layer.

Specific examples of the "aromatic hydrocarbon group", the "aromatic heterocyclic group" or the "condensed polycyclic aromatic group" in the "carbon atom having a substituted or unsubstituted aromatic hydrocarbon group", the "carbon atom having a substituted or unsubstituted aromatic heterocyclic group" or the "carbon atom having a substituted or unsubstituted condensed polycyclic aromatic group", which is represented by $X_1$ and $X_2$ in the general formula (1), include: a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, a isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, a carborinyl group, and the like. In addition, it can be selected from an aryl group having a carbon number of 6 to 30 and a heteroaryl group having a carbon number of 2 to 30. The substituent and the substituted benzene ring or the plurality of substituents substituted with the same benzene rings may be bonded to each other via a single bond, a substituted or unsubstituted methylene group, a substituted or unsubstituted amino group, an oxygen atom, or a sulfur atom, to form a ring.

Specific examples of the "linear or branched alkyl group having a carbon number of 1 to 6", the "cycloalkyl group having a carbon number of 5 to 10" or the "linear or branched alkenyl group having a carbon number of 2 to 6" in the "carbon atom having a linear or branched alkyl group having a carbon number of 1 to 6 which may have a substituent", the "carbon atom having a cycloalkyl group having a carbon number of 5 to 10 which may have a substituent" or the "carbon atom having a linear or branched alkenyl group having a carbon number of 2 to 6 which may have a substituent", which is represented by $X_1$ and $X_2$ in the general formula (1), include: a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group. In addition, the substituent and the substituted benzene ring or the plurality of substituents substituted with the same benzene rings may be bonded to each other via a single bond, a substituted or unsubstituted methylene group, a substituted or unsubstituted amino group, an oxygen atom, or a sulfur atom, to form a ring.

Specific examples of the "linear or branched alkyloxy group having a carbon number of 1 to 6" or the "cycloalkyloxy group having a carbon number of 5 to 10" in the "carbon atom having a linear or branched alkyloxy group having a carbon number of 1 to 6 which may have a substituent" or the "carbon atom having a cycloalkyloxy group having a carbon number of 5 to 10 which may have a substituent", which is represented by $X_1$ and $X_2$ in the general formula (1), include: a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, a 2-adamantyloxy group, and the like. In addition, the substituent and the substituted benzene ring or the plurality of substituents substituted with the same benzene rings may be bonded to each other via a single bond, a substituted or unsubstituted methylene group, a substituted or unsubstituted amino group, an oxygen atom, or a sulfur atom, to form a ring.

Specific examples of the "substituent" in the "carbon atom having a substituted aromatic hydrocarbon group", the "carbon atom having a substituted aromatic heterocyclic group", the "carbon atom having a substituted condensed polycyclic aromatic group", the "carbon atom having a linear or branched alkyl group having a carbon number of 1 to 6 which may have a substituent", the "carbon atom having a cycloalkyl group having a carbon number of 5 to 10 which may have a substituent", the "carbon atom having a linear or branched alkenyl group having a carbon number of 2 to 6 which may have a substituent", the "carbon atom having a linear or branched alkyloxy group having a carbon number of 1 to 6 which may have a substituent", or the "carbon atom having a cycloalkyloxy group having a carbon number of 5 to 10 which may have a substituent", which is represented by $X_1$ and $X_2$ in the general formula (1), include: a deuterium atom, a cyano group, a nitro group; halogen atoms such as a fluorine atom, a chlorine atom, a bromine atom, and an iodine atom; silyl groups such as a trimethyl silyl group and a triphenyl silyl group; a linear or branched alkyl group having a carbon number of 1 to 6 such as a methyl group, an ethyl group and a propyl group; a linear or branched alkyloxy group having a carbon number of 1 to 6 such as a methyloxy group, an ethyloxy group and a propyloxy group; alkenyl groups such as a vinyl group and an allyl group; aryloxy groups such as a phenyloxy group and a tolyloxy group; aryl alkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, and a triphenylenyl group; aromatic heterocyclic groups such as a pyridyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carborinyl group; and the like. These substituents may be further substituted with the substituents exemplified above. In addition, the substituent and the substituted benzene ring or the plurality of substituents substituted with the same benzene rings may be bonded to each other via a single bond, a substituted or unsubstituted methylene group, a substituted or unsubstituted amino group, an oxygen atom, or a sulfur atom, to form a ring.

Examples of the "aromatic hydrocarbon group", the "aromatic heterocyclic group" or the "condensed polycyclic aromatic group" in the "substituted or unsubstituted aromatic hydrocarbon group", the "substituted or unsubstituted aromatic heterocyclic group" or the "substituted or unsubstituted condensed polycyclic aromatic group", which is represented by Ar in the general formulae (1) to (5), include the same groups as those shown for the "aromatic hydrocarbon group", the "aromatic heterocyclic group" or the "condensed polycyclic aromatic group" in $X_1$ and $X_2$ in the general formula (1), and also the same aspects can be mentioned as aspects that can be taken.

Examples of the "substituent" in the "substituted aromatic hydrocarbon group", the "substituted aromatic heterocyclic group" or the "substituted condensed polycyclic aromatic group", which is represented by Ar in the general formulae (1) to (5), include the same groups as those shown for the "substituent" in $X_1$ and $X_2$ in the general formula (1), and also the same aspects can be mentioned as aspects that can be taken.

Examples of the "aromatic hydrocarbon group", the "aromatic heterocyclic group" or the "condensed polycyclic aromatic group" in the "substituted or unsubstituted aromatic hydrocarbon group", the "substituted or unsubstituted aromatic heterocyclic group" or the "substituted or unsubstituted condensed polycyclic aromatic group", which is represented by $R_1$ to $R_{14}$ in the general formulae (1) to (5), include the same groups as those shown for the "aromatic hydrocarbon group", the "aromatic heterocyclic group" or the "condensed polycyclic aromatic group" in $X_1$ or $X_2$ in the general formula (1), and also the same aspects can be mentioned as aspects that can be taken.

Examples of the "linear or branched alkyl group having a carbon number of 1 to 6", the "cycloalkyl group having a carbon number of 5 to 10" or the "linear or branched alkenyl group having a carbon number of 2 to 6" in the "linear or branched alkyl group having a carbon number of 1 to 6 which may have a substituent", the "cycloalkyl group having a carbon number of 5 to 10 which may have a substituent" or the "linear or branched alkenyl group having a carbon number of 2 to 6 which may have a substituent", which is represented by $R_1$ to $R_{14}$ in the general formulae (1) to (5), include the same groups as those shown for the "linear or branched alkyl group having a carbon number of 1 to 6", the "cycloalkyl group having a carbon number of 5 to 10" or the "linear or branched alkenyl group having a carbon number of 2 to 6" in $X_1$ or $X_2$ in the general formula (1), and also the same aspects can be mentioned as aspects that can be taken.

Examples of the "linear or branched alkyloxy group having a carbon number of 1 to 6" or the "cycloalkyloxy group having a carbon number of 5 to 10" in the "linear or branched alkyloxy group having a carbon number of 1 to 6 which may have a substituent" or the "cycloalkyloxy group having a carbon number of 5 to 10 which may have a substituent", which is represented by $R_1$ to $R_{14}$ in the general formulae (1) to (5), include the same groups as those shown for the "linear or branched alkyloxy group having a carbon number of 1 to 6" or the "cycloalkyl group having a carbon number of 5 to 10" in $X_1$ or $X_2$ in the general formula (1), and also the same aspects can be mentioned as aspects that can be taken.

Examples of the "substituent" in the "substituted aromatic hydrocarbon group", the "substituted aromatic heterocyclic group", the "substituted condensed polycyclic aromatic group", the "linear or branched alkyl group having a carbon number of 1 to 6 which may have a substituent", the "cycloalkyl group having a carbon number of 5 to 10 which may have a substituent", the "linear or branched alkenyl group having a carbon number of 2 to 6 which may have a substituent", the "linear or branched alkyloxy group having a carbon number of 1 to 6 which may have a substituent", or the "cycloalkyloxy group having a carbon number of 5 to 10 which may have a substituent", which is represented by $R_1$ to $R_{14}$ in the general formulae (1) to (5), include the same groups as those shown for the "substituent" in $X_1$ and $X_2$ in the general formula (1), and also the same aspects can be mentioned as aspects that can be taken.

m in the general formulae (1) to (5) is preferably represented by an integer of 1 or 2, preferably an integer of 2. In the case where m is an integer of 2 or more, at least two of two or more Ar's are preferably different from each other.

The compounds having a benzimidazole ring structure represented by the general formulae (1) to (5) suitably used for the organic EL device of the present embodiment can be used as a constituent material of an electron injection layer, an electron transport layer, a hole blocking layer, or a light emitting layer of the organic EL device. These compounds have high electron mobility and are preferable as a material of the electron injection layer or the electron transport layer.

The organic EL device of the present embodiment uses a material for the organic EL device, having excellent electron injection and transport performance, and excellent stability and durability of thin film. Therefore, it is possible to improve electron transport efficiency from an electron transport layer to a light emitting layer, improve a luminous efficiency, reduce a drive voltage, and improve the durability of the organic EL device, as compared with a conventional organic EL device. Accordingly, an organic EL device having high efficiency, a low drive voltage and a long lifetime can be achieved.

Specific examples of a preferable compound among the compounds having a benzimidazole ring structure represented by the general formula (1), which are suitably used in the organic EL device of the present embodiment, are shown below, but the present invention is not limited to these compounds.

[Chem. 7]
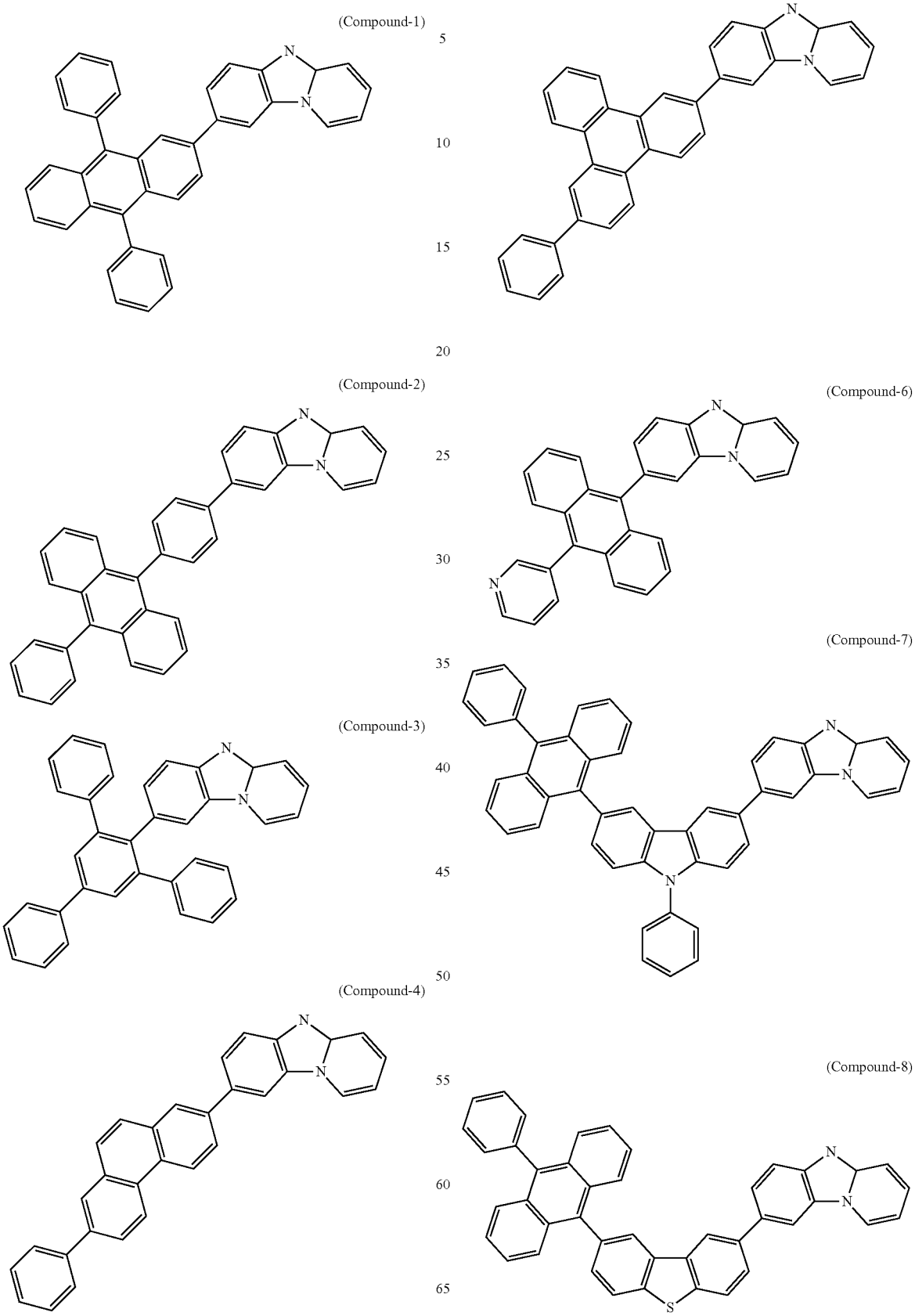

(Compound-9)
(Compound-14)
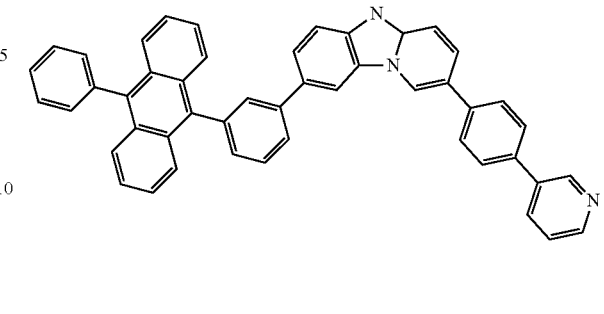
(Compound-10)
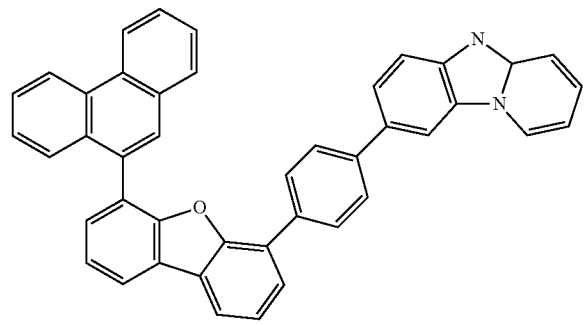
(Compound-15)
(Compound-11)
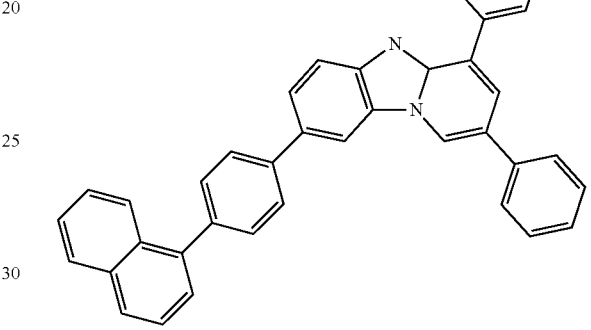
(Compound-16)
(Compound-12)
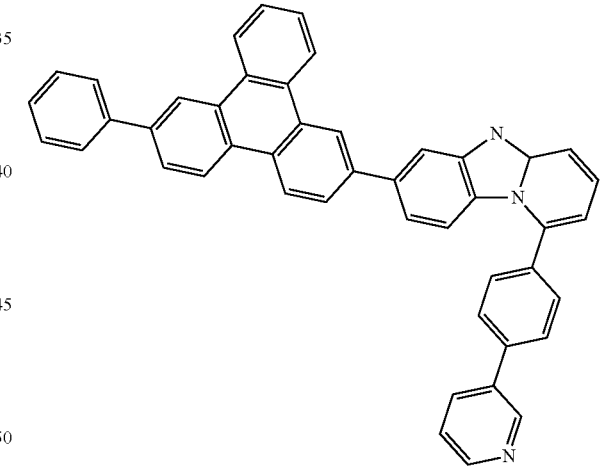
(Compound-13)
(Compound-17)
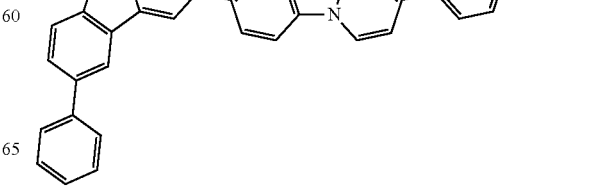

(Compound-18)
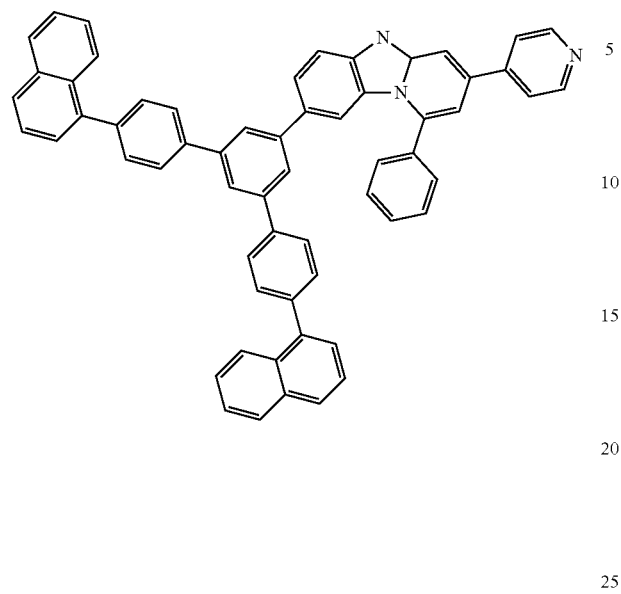
(Compound-19)
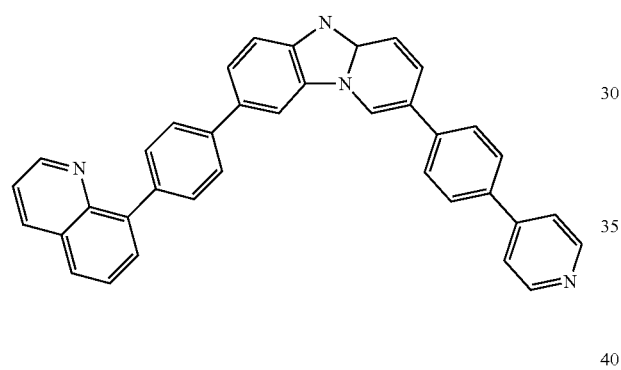
(Compound-20)
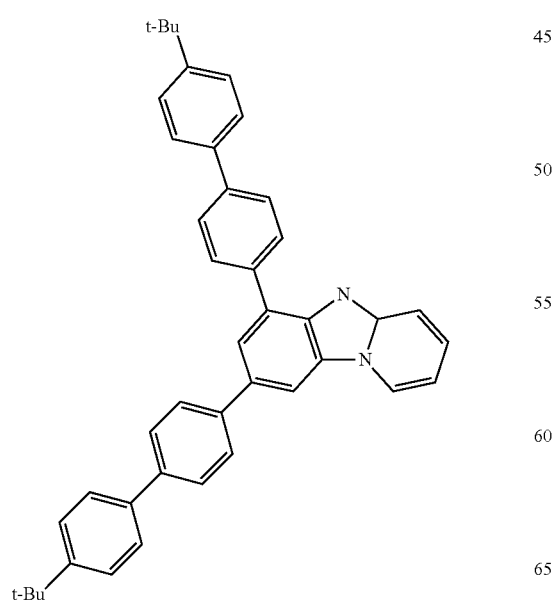
(Compound-21)
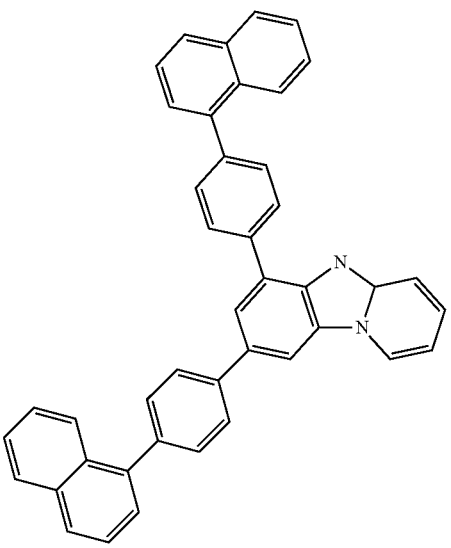
[Chem. 8]
(Compound-22)
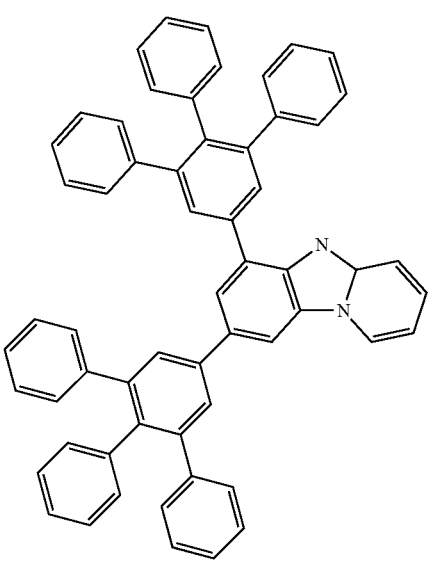

(Compound-23)
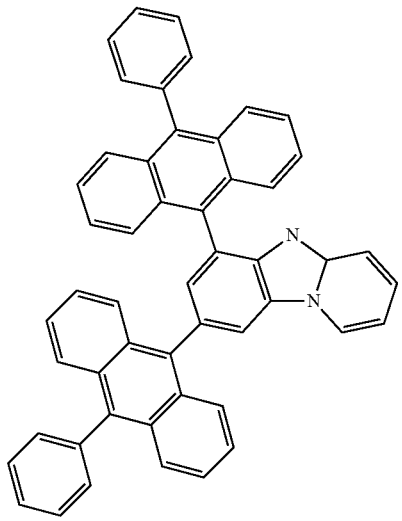
(Compound-24)
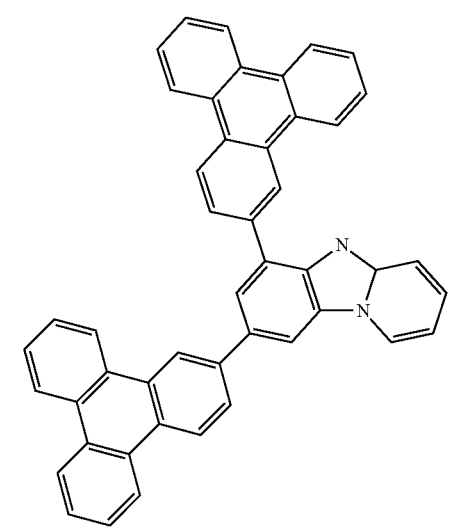
(Compound-25)
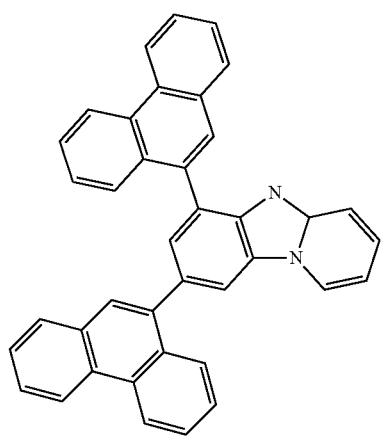
(Compound-26)
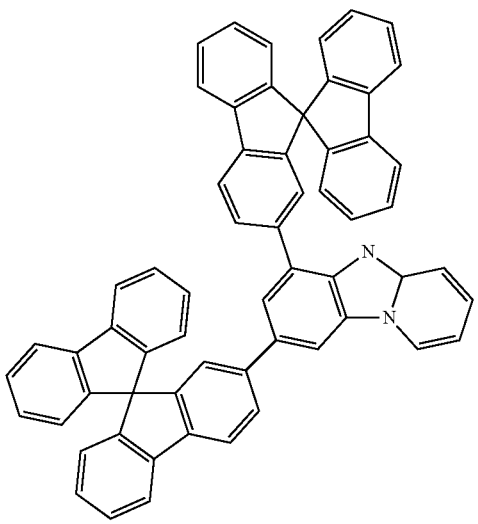
(Compound-27)
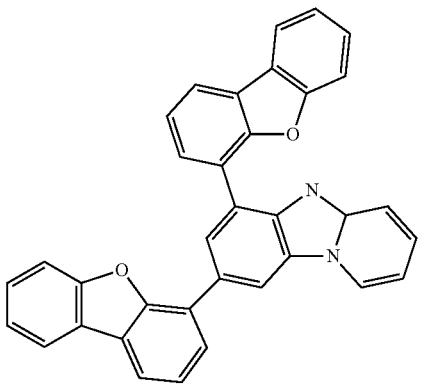
(Compound-28)
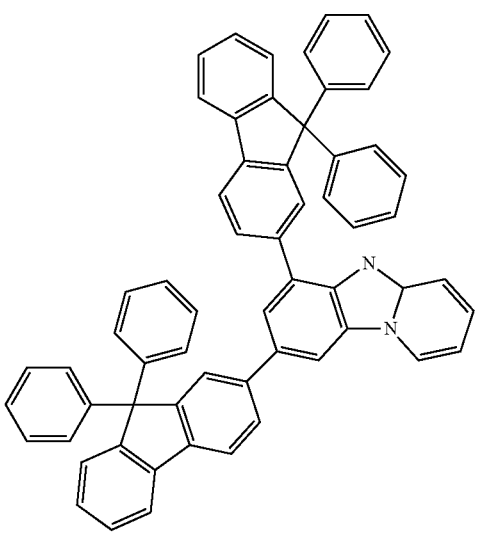

(Compound-29)
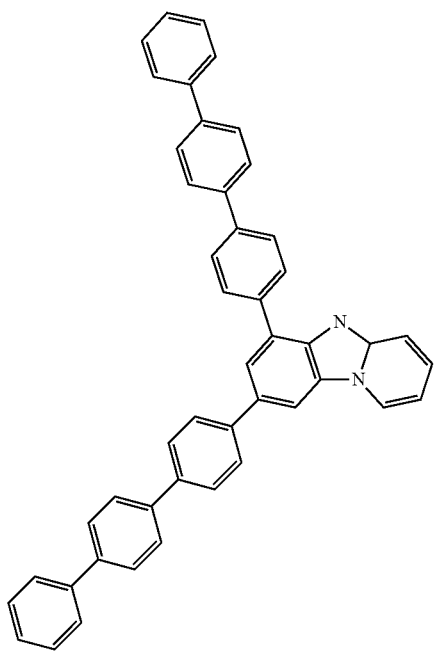
(Compound-30)
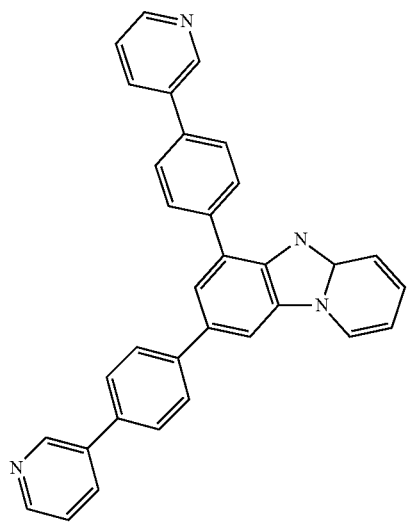
(Compound-31)
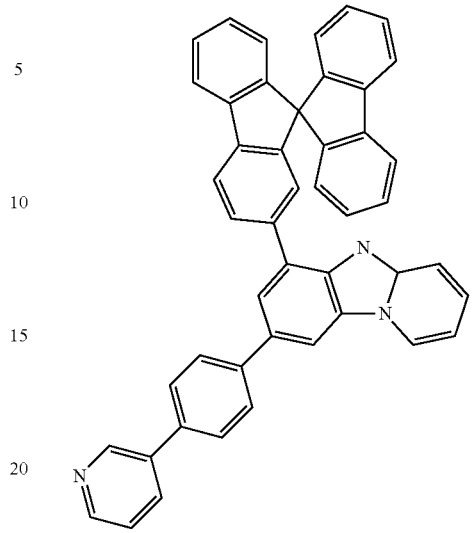
(Compound-32)
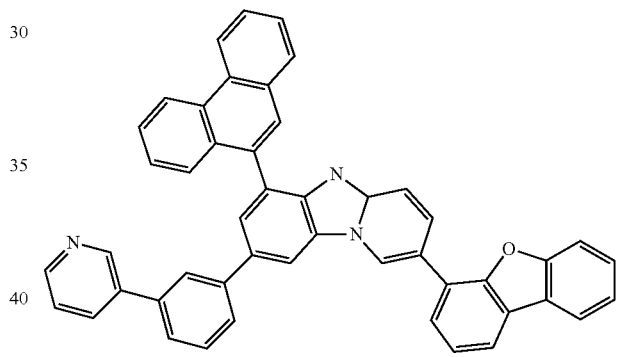
(Compound-33)
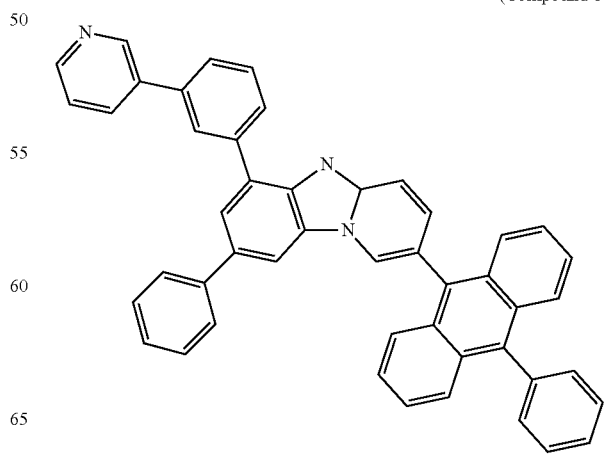

(Compound-34)
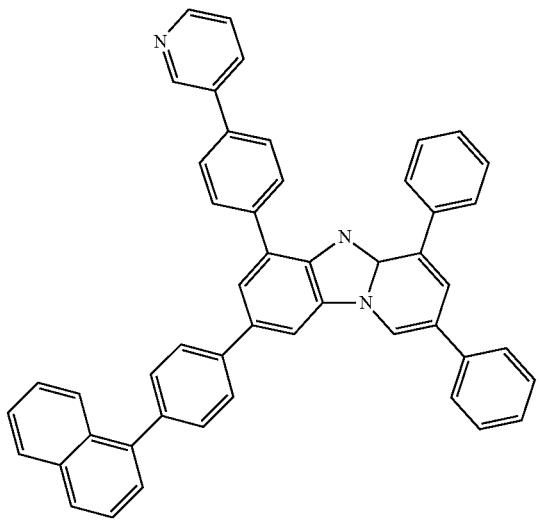
(Compound-35)
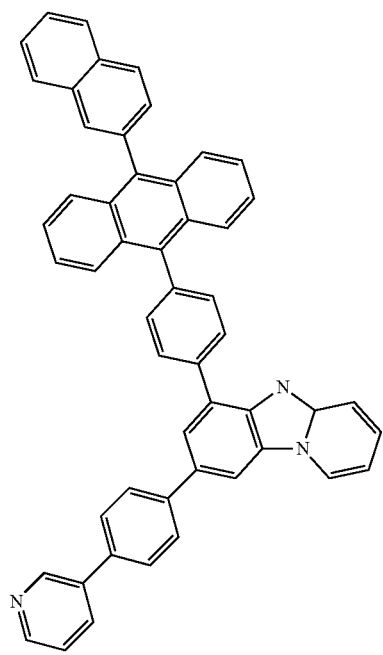
(Compound-36)
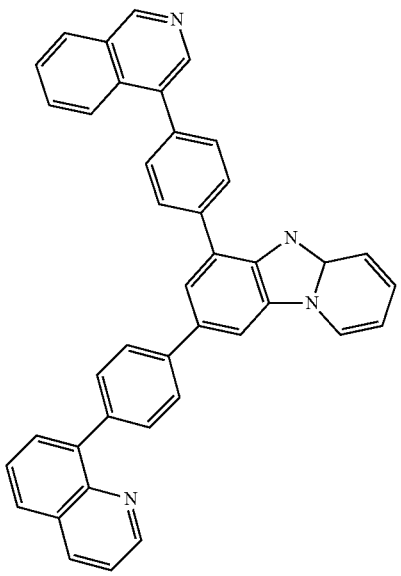
(Compound-37)
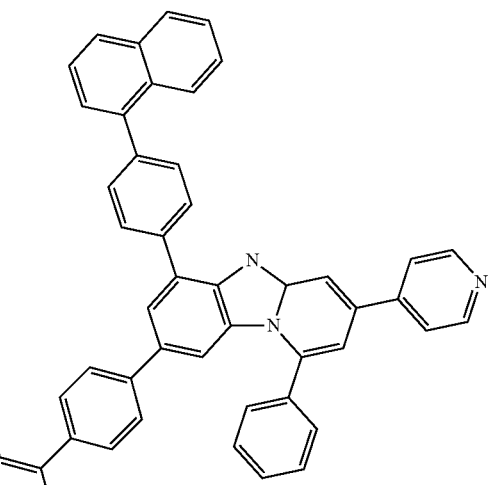

-continued
(Compound-38)
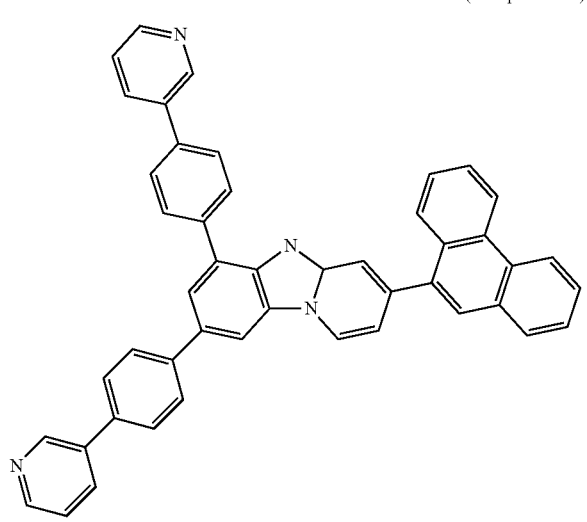
(Compound-39)
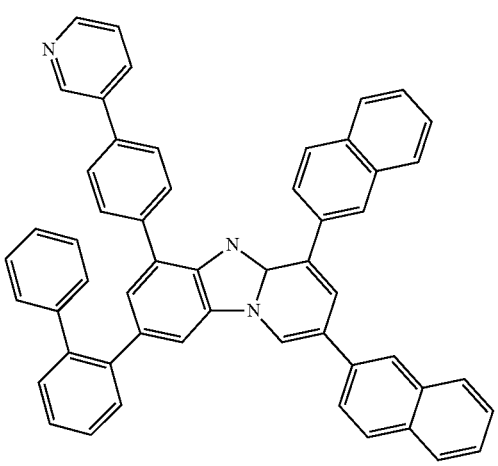
(Compound-40)
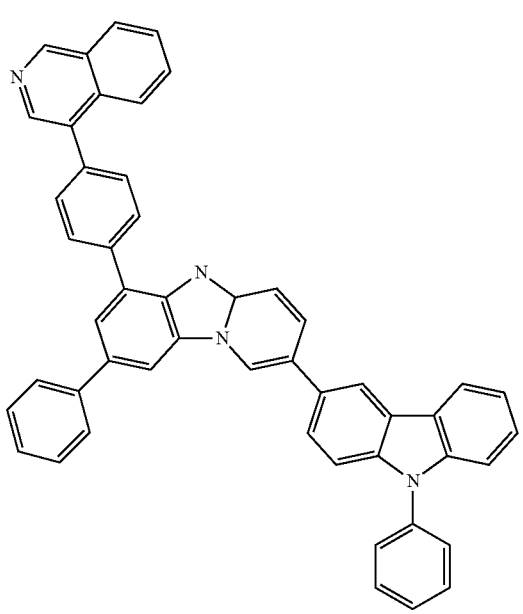
(Compound-41)
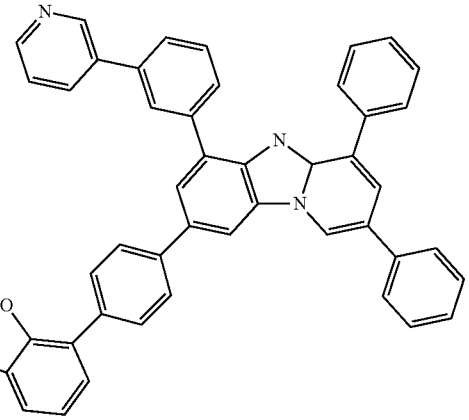
(Compound-42)
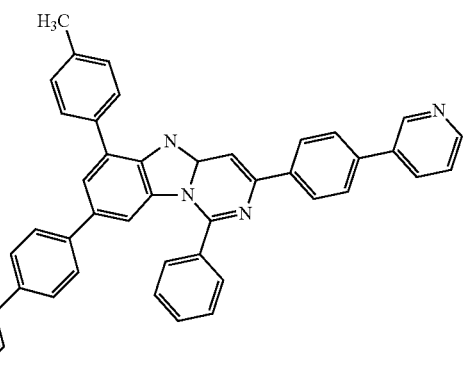
(Compound-43)
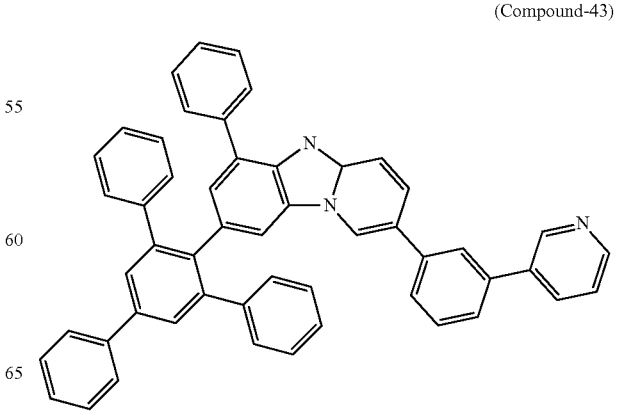

-continued
(Compound-44)
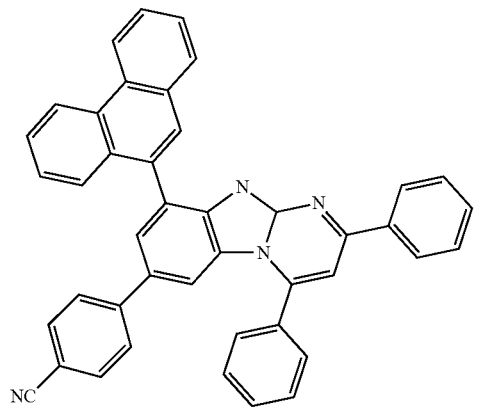
(Compound-45)
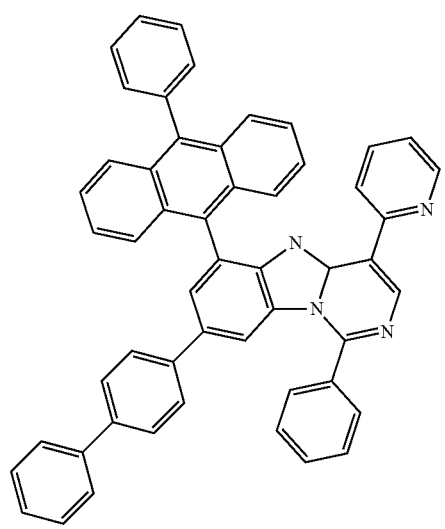
(Compound-46)
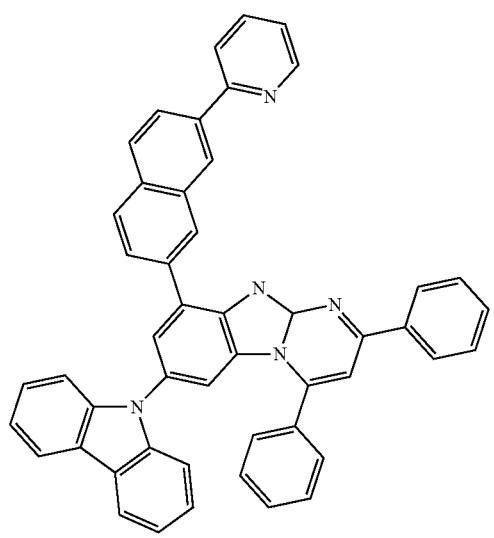
(Compound-47)
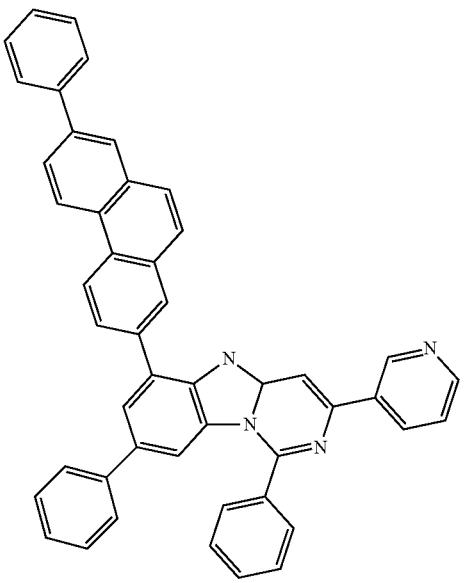
(Compound-48)
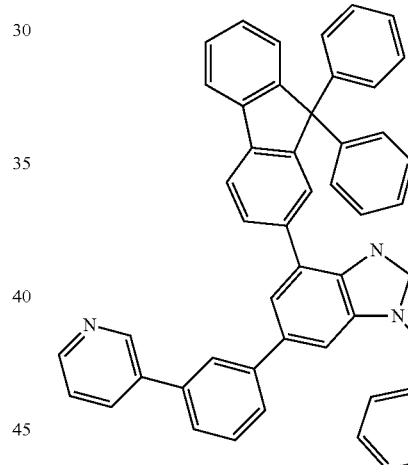
(Compound-49)
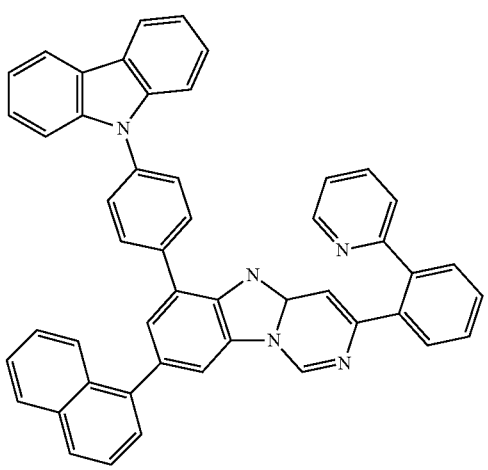

-continued
(Compound-50)
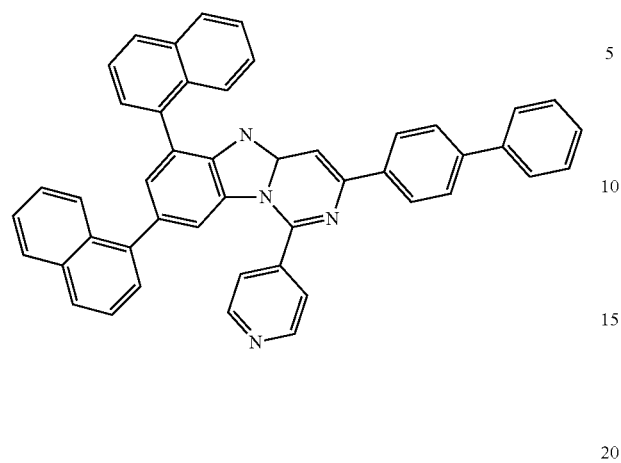
(Compound-51)
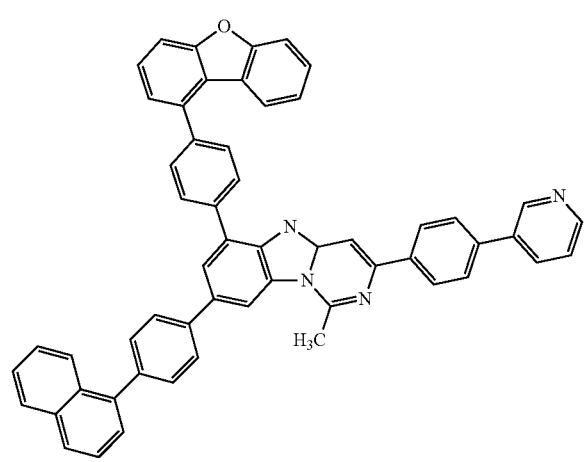
(Compound-52)
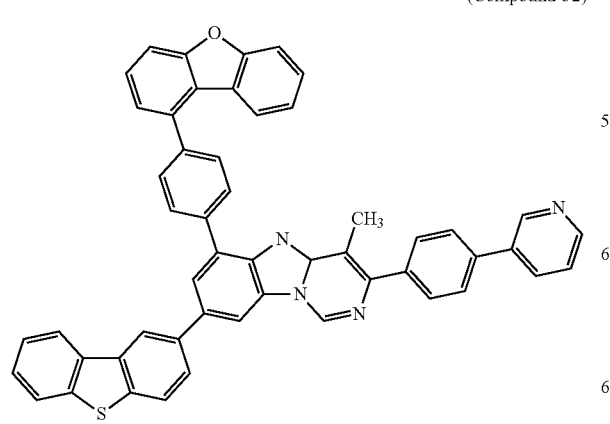
-continued
(Compound-53)
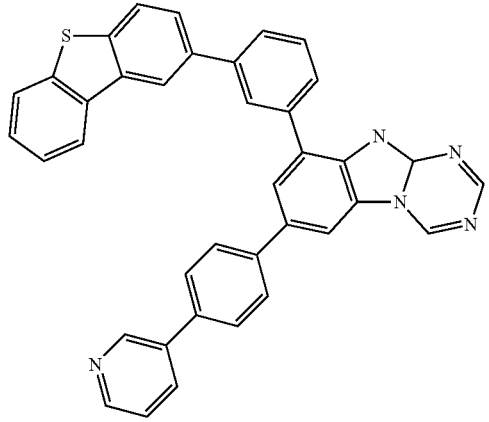
(Compound-54)
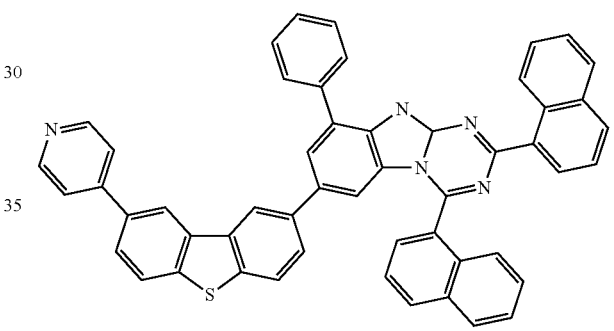
(Compound-55)
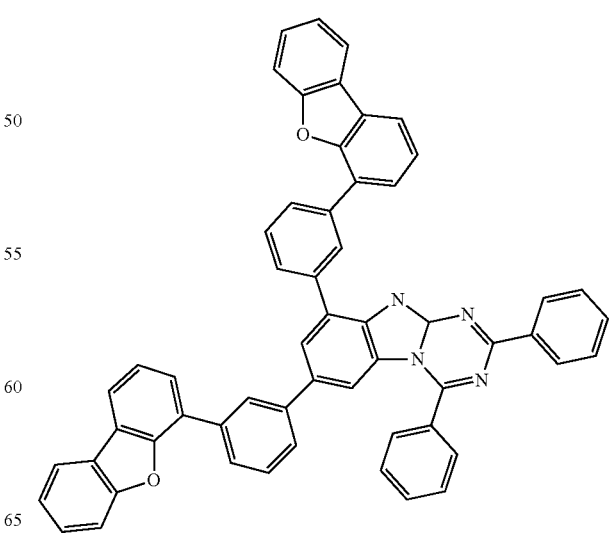

[Chem. 10]
(Compound-56)
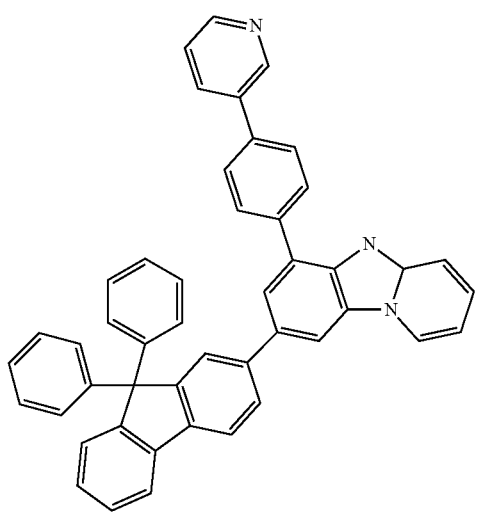
(Compound-57)
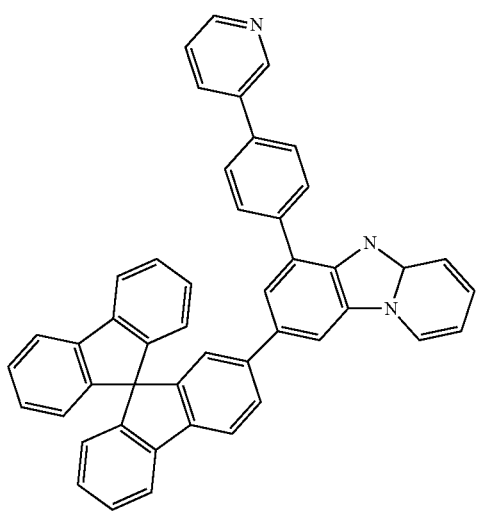
(Compound-58)
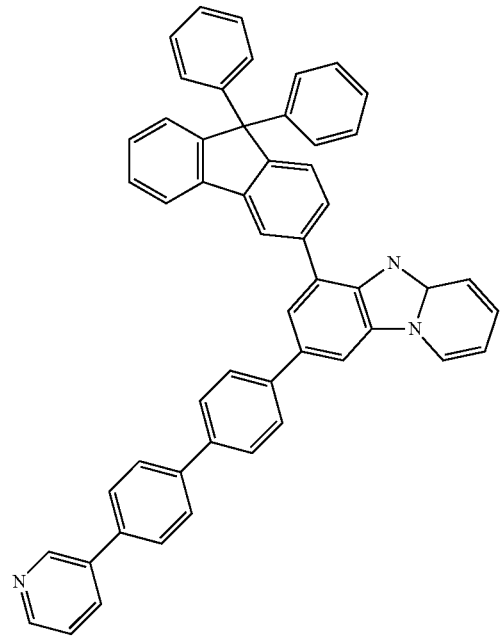
(Compound-59)
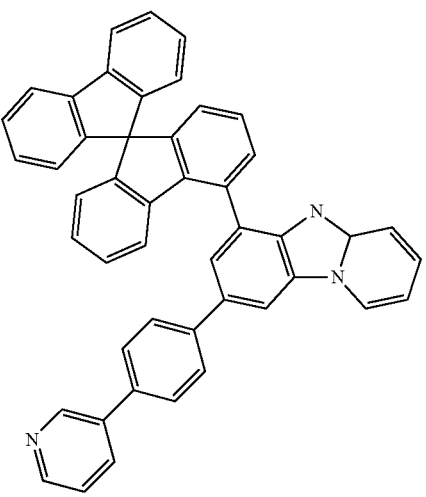

(Compound-60)
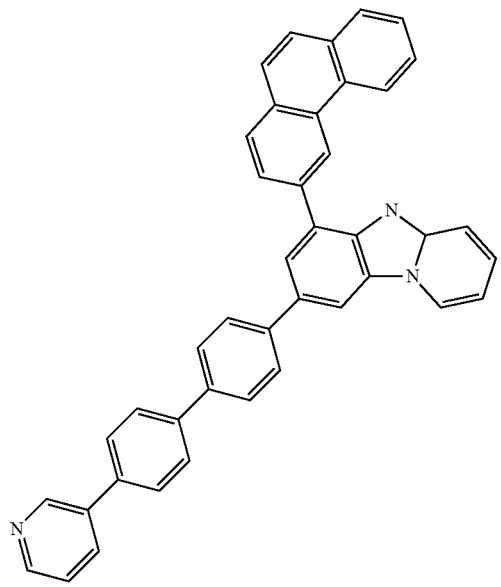
(Compound-61)
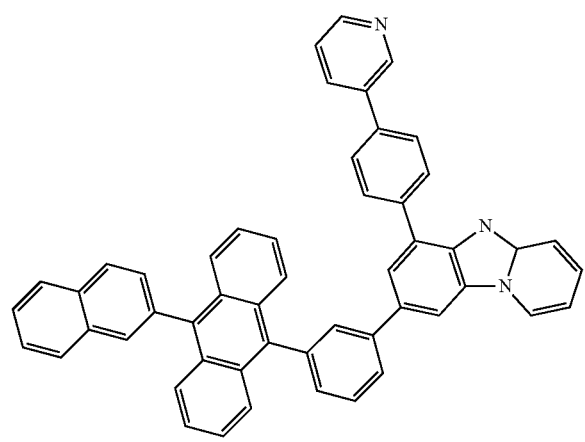
(Compound-62)
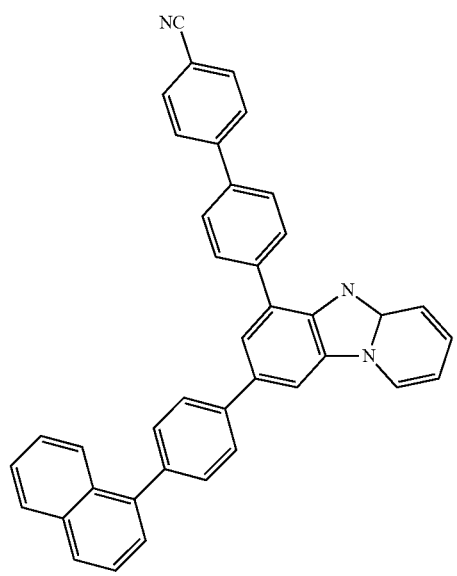
(Compound-63)
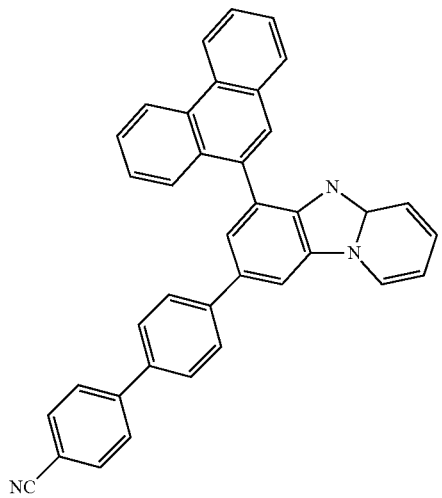
(Compound-64)
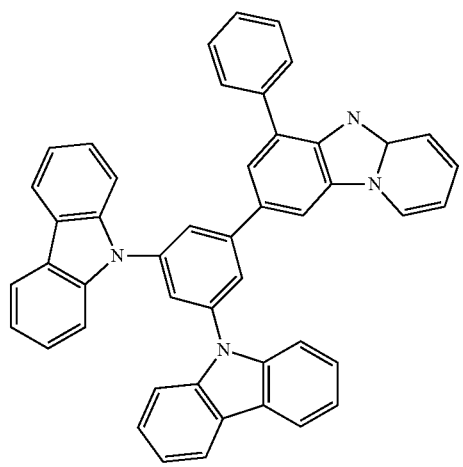
(Compound-65)
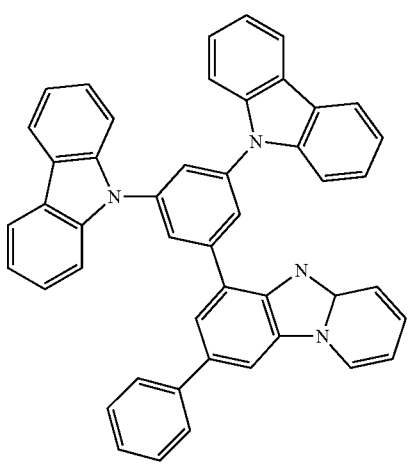

(Compound-66)
(Compound-67)
(Compound-68)
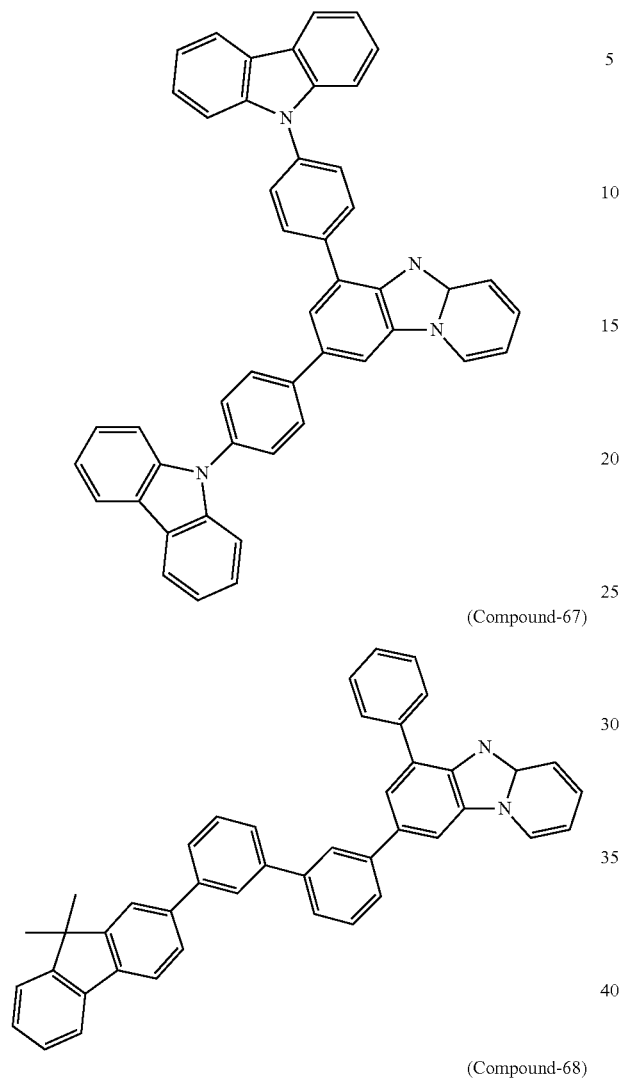
(Compound-69)
(Compound-70)
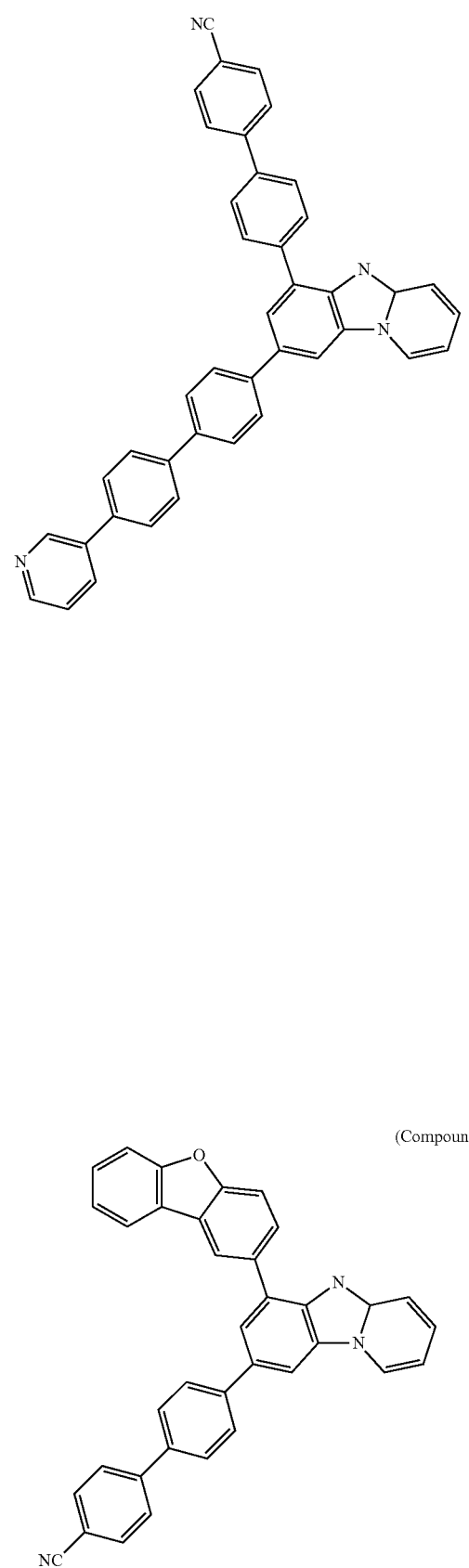

(Compound-71)
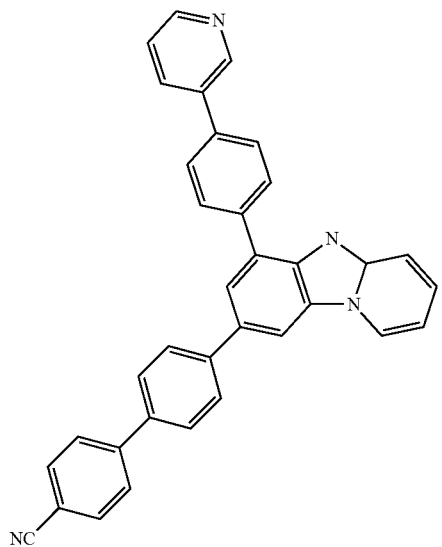
[Chem. 11]
(Compound-72)
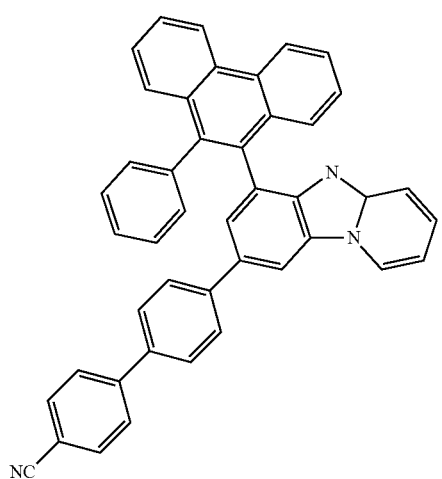
(Compound-73)
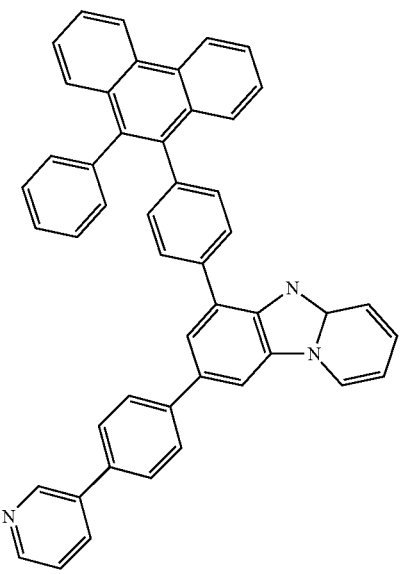
(Compound-74)
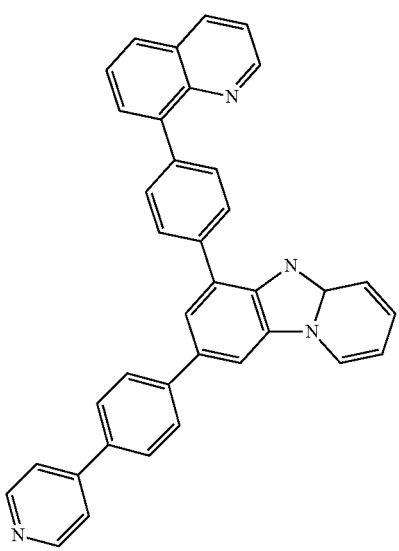

(Compound-75)

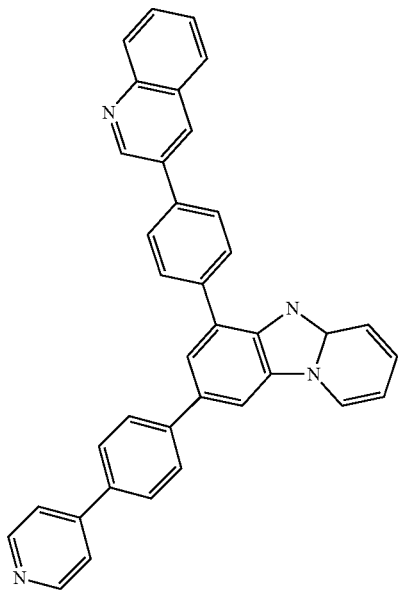

The compounds having a benzimidazole ring structure represented by the general formula (1) of the present embodiment are new compounds. These compounds can be synthesized in accordance with a publicly known method itself, for example, as to be described below (see, e.g., Non-Patent Literatures 6 and 7).

[Chem. 12]

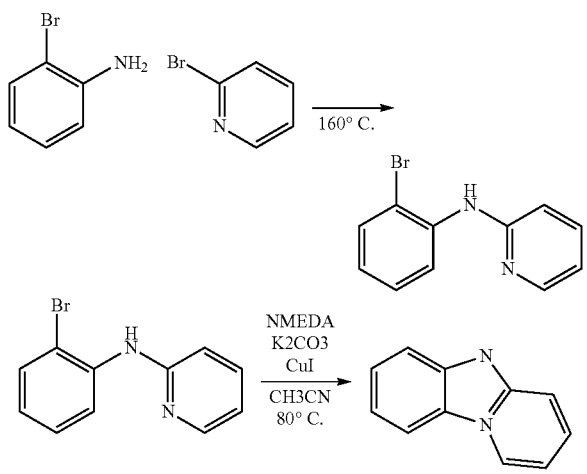

Purification of the compounds having a benzimidazole ring structure represented by the general formulae (1) to (5) is performed by purification using chromatograph, adsorption purification using silica gel, activated carbon, activated clay, or the like, recrystallization and crystallization using a solvent, sublimation purification, or the like. The compound is identified by NMR analysis. A melting point, a glass transition point (Tg) and a work function are measured as physical property values. The melting point is an index of a vapor deposition property, the glass transition point (Tg) is an index of stability of the thin film state, and the work function is an index of a hole transport property and a hole blocking property.

The melting point and the glass transition point (Tg) are measured with a high sensitivity differential scanning calorimeter (DSC 3100 SA, manufactured by Bruker AXS GmbH) by using a powder of the compounds. The melting point of the compounds having a benzimidazole ring structure represented by the general formulae (1) to (5) is not particularly limited, but is preferably 200° C. or higher. The upper limit of the melting point is not particularly limited and, for example, a compound having a melting point of 400° C. or lower can be adopted. The glass transition point of the compounds having a benzimidazole ring structure represented by the general formulae (1) to (5) is not particularly limited, but is preferably 100° C. or higher in view of the stability of the formed thin film. The upper limit of the glass transition point is not particularly limited and, for example, a compound having a glass transition point of 250° C. or lower can be adopted.

The work function is determined by producing a thin film of 100 nm on an ITO substrate and measuring with an ionization potential measuring device (PYS-202, manufactured by Sumitomo Heavy Industries, Ltd.). The work function of the vapor deposition film having a film thickness of 100 nm produced on an ITO substrate by using the compounds having a benzimidazole ring structure represented by the general formulae (1) to (5) is not particularly limited, but is preferably greater than 5.5 eV. The upper limit of the work function of the vapor deposition film is not particularly limited and, for example, a vapor deposition film having a work function of 6.5 eV or lower can be adopted.

Examples of the structure of the organic EL device of the present embodiment include a structure having an anode, a hole injection layer, a hole transport layer, a light emitting layer, an electron transport layer, an electron injection layer, and a cathode in this order on a substrate, a structure further including an electron blocking layer between the hole transport layer and the light emitting layer, and a structure further including a hole blocking layer between the light emitting layer and the electron transport layer. In these multilayer structures, some of organic layers can be omitted or combined, and examples thereof include: a configuration in which the hole injection layer and the hole transport layer are combined; a configuration in which the electronic injection layer and the electron transport layer are combined; a configuration in which the hole transport layer and the electron blocking layer are combined; a configuration in which the electron transport layer and the hole blocking layer are combined, and the like. A configuration in which two or more organic layers having the same function are laminated can be used, and examples thereof include a configuration in which two hole transport layers are laminated; a configuration in which two light emitting layers are laminated; a configuration in which two electron transport layers are laminated; and the like.

As an anode of the organic EL device of the present embodiment, an electrode material having a large work function, such as ITO or gold is used.

As the hole injection layer of the organic EL device of the present embodiment, use can be made of a porphyrin compound represented by copper phthalocyanine, a star burst type triphenylamine derivative, an arylamine compound having two or more triphenylamine structures or carbazolyl structures in the molecule and having a structure where these structures are connected by a single bond or a divalent group not containing a hetero atom, and the like. In addition, a heterocyclic compound having acceptor properties, such as hexacyano azatriphenylene, or a coating-type polymer material can be used. These materials can form a thin film by a publicly known method such as a spin coating method or an ink jet method in addition to a deposition method.

As the hole transport layer of the organic EL device of the present embodiment, use can be made of benzidine derivatives such as N,N'-diphenyl-N,N'-di(m-tolyl) benzidine (hereinafter abbreviated as TPD), N,N'-diphenyl-N,N'-di(α-naphthyl) benzidine (hereinafter referred to as NPD) and N,N,N',N'-tetrabiphenylyl benzidine, 1,1-bis[(di-4-tolyl amino) phenyl]cyclohexane (hereinafter abbreviated as TAPC), an aryl amine compound having two or more triphenylamine structures or carbazolyl structures in the molecule and having a structure where these structures are connected by a single bond or a divalent group not containing a hetero atom, such as N,N,N',N'-tetrabiphenylyl benzidine, and the like. These may be used to form a film alone or may be used as a single layer formed by being mixed with another material, or may be used as a laminated structure of layers each formed alone using the plurality of materials, layers each formed by being mixed using the plurality of materials, or a layer formed alone and a layer formed by being mixed, using the plurality of materials. As a hole injection and transport layer, a coating type polymer material such as poly(3,4-ethylene dioxythiophene) (hereinafter abbreviated as PEDOT)/poly(styrene sulfonate) (hereinafter abbreviated as PSS) can be used. These materials can form a thin film by a publicly known method such as a spin coating method or an ink jet method in addition to a deposition method.

In addition, in the hole injection layer or the hole transport layer, a material that is generally used for these layers and is further P-doped with trisbromo phenyl amine hexachloro antimony, a radialene derivative (see, e.g., Patent Literature 5), and a polymer compound having a structure of a benzidine derivative such as TPD in a partial structure thereof can be used.

As the electron blocking layer of the organic EL device of the present embodiment, use can be made of a compound having an electron blocking action, such as carbazole derivatives such as 4,4',4"-tri(N-carbazolyl) triphenyl amine (hereinafter abbreviated as TCTA), 9,9-bis[4-(carbazole-9-yl) phenyl]fluorene, 1,3-bis(carbazole-9-yl) benzene (hereinafter abbreviated as mCP), and 2,2-bis(4-carbazole-9-yl-phenyl) adamantane (hereinafter abbreviated as Ad-Cz), and compounds having a triphenyl silyl group and a triaryl amine structure represented by 9-[4-(carbazole-9-yl) phenyl]-9-[4-(triphenyl silyl) phenyl]-9H-fluorene. These may be used to form a film alone or may be used as a single layer formed by being mixed with another material, or may be used as a laminated structure of layers each formed alone using the plurality of materials, layers each formed by being mixed using the plurality of materials, or a layer formed alone and a layer formed by being mixed, using the plurality of materials. These materials can form a thin film by a publicly known method such as a spin coating method or an ink jet method in addition to a deposition method.

As the light emitting layer of the organic EL device of the present embodiment, use can be made of, in addition to the compound having a benzimidazole ring structure of the present embodiment, metal complexes of quinolinol derivatives as typified by $Alq_3$, various metal complexes, anthracene derivatives, bisstyryl benzene derivatives, pyrene derivatives, oxazole derivatives, polyparaphenylene vinylene derivatives, and the like. The light emitting layer may be constituted by a host material and a dopant material. As the host material, the anthracene derivatives are preferably used, and in addition to the light emitting materials such as the compound having a benzimidazole ring structure of the present embodiment, heterocyclic compounds having an indole ring as a partial structure of a condensed ring, heterocyclic compounds having an carbazole ring as a partial structure of a condensed ring, carbazole derivatives, thiazole derivatives, benzimidazole derivatives, polydialkyl fluorene derivatives, and the like can be also used. As the dopant material, quinacridone, coumarin, rubrene, perylene, and derivatives thereof, benzopyran derivatives, rhodamine derivatives, amino styryl derivatives, and the like can be used. These may be used to form a film alone or may be used as a single layer formed by being mixed with another material, or may be used as a laminated structure of layers each formed alone using the plurality of materials, layers each formed by being mixed using the plurality of materials, or a layer formed alone and a layer formed by being mixed, using the plurality of materials.

A phosphorescence emitter can also be used as the light emitting material. As the phosphorescence emitter, a phosphorescence emitter of a metal complex of iridium, platinum or the like can be used. Green phosphorescence emitters such as $Ir(ppy)_3$, blue phosphorescence emitters such as FIrpic and FIr6, red phosphorescence emitters such as $Btp_2Ir$ (acac), and the like can be used. As the host material at this time, carbazole derivatives such as 4,4'-di(N-carbazolyl) biphenyl (hereinafter abbreviated as CBP), TCTA and mCP, as well as the compound having the benzazole ring structure and a pyridindole ring structure of the present embodiment can be used as the host material having hole injection and transport properties. As the electron transport host material, p-bis(triphenyl silyl) benzene (hereinafter abbreviated as UGH2), 2,2',2"-(1,3,5-phenylene)-tris(1-phenyl-1H-benzimidazole) (hereinafter abbreviated as TPBI) and the like can be used, and an organic EL device having a high performance can be produced.

In order to avoid concentration quenching, doping of the phosphorescent emitting material into the host material is preferably performed by co-deposition in a range of 1 to 30 weight percents with respect to the entire light emitting layer.

It is also possible to use materials that emit delayed fluorescence, such as PIC-TRZ, CC2TA, PXZ-TRZ, and CDCB derivatives such as 4CzIPN as the light emitting material (see, e.g., Non-Patent Literature 3). These materials can form a thin film by a publicly known method such as a spin coating method or an ink jet method in addition to a deposition method.

As the hole blocking layer of the organic EL device of the present embodiment, in addition to the compound having a benzimidazole ring structure of the present embodiment, use can be made of compounds having a hole blocking effect such as phenanthroline derivatives such as BCP, metal complexes of quinolinol derivatives such as aluminum (III) bis(2-methyl-8-quinolinate)-4-phenyl phenolate (hereinafter abbreviated as BAlq), various rare earth complexes, oxazole derivatives, triazole derivatives, triazine derivatives, pyrimidine derivatives, oxadiazole derivatives, benzazole derivatives, and the like. These materials may also double as materials of the electron transport layer. These may be used to form a film alone or may be used as a single layer formed by being mixed with another material, or may be used as a laminated structure of layers each formed alone using the plurality of materials, layers each formed by being mixed using the plurality of materials, or a layer formed alone and a layer formed by being mixed, using the plurality of materials. These materials can form a thin film by a publicly known method such as a spin coating method or an ink jet method in addition to a deposition method. In the case where the compound having a benzimidazole ring structure of the present embodiment is used in combination with other materials, the mixing ratio thereof is not particularly limited, but can be set as, for example, the compound having a benzimidazole ring structure of the present embodiment: other materials=100:1 to 1:100, and preferably the compound having a benzimidazole ring structure of the present embodiment:other materials=100:1 to 1:4.

As the electron transport layer of the organic EL device of the present embodiment, in addition to the compound having a benzimidazole ring structure of the present embodiment, use can be made of metal complexes of quinolinol derivatives as typified by Alq$_3$ and BAlq, various metal complexes, triazole derivatives, triazine derivatives, pyrimidine derivatives, oxadiazole derivatives, pyridine derivatives, benzimidazole derivatives, benzazole derivatives, thiadiazole derivatives, anthracene derivatives, carbodiimide derivatives, quinoxaline derivatives, pyridindole derivatives, phenanthroline derivatives, silole derivatives, and the like. These may be used to form a film alone or may be used as a single layer formed by being mixed with another material, or may be used as a laminated structure of layers each formed alone using the plurality of materials, layers each formed by being mixed using the plurality of materials, or a layer formed alone and a layer formed by being mixed, using the plurality of materials. These materials can form a thin film by a publicly known method such as a spin coating method or an ink jet method in addition to a deposition method. In the case where the compound having a benzimidazole ring structure of the present embodiment is used in combination with other materials, the mixing ratio thereof is not particularly limited, but can be set as, for example, the compound having a benzimidazole ring structure of the present embodiment:other materials=100:1 to 1:100, and preferably the compound having a benzimidazole ring structure of the present embodiment:other materials=100:1 to 1:4.

As the electron injection layer of the organic EL device of the present embodiment, in addition to the compound having a benzimidazole ring structure of the present embodiment, use can be made of alkali metal salts such as lithium fluoride and cesium fluoride, alkaline earth metal salts such as magnesium fluoride, metal complexes of quinolinol derivatives such as lithium quinolinol, metal oxides such as aluminum oxide, metals such as ytterbium (Yb), samarium (Sm), calcium (Ca), strontium (Sr), and cesium (Cs), and the like, but this can be omitted in a preferred selection of the electron transport layer and the cathode.

Furthermore, in the electron injection layer or the electron transport layer, it is possible to use a material that is generally used for these layers and is further N-doped with a metal such as cesium.

As the cathode of the organic EL device of the present embodiment, an electrode material having a low work function such as aluminum, an alloy having a lower work function such as a magnesium silver alloy, a magnesium calcium alloy, a magnesium indium alloy, or an aluminum magnesium alloy, ITO, IZO, and the like can be used as an electrode material.

The embodiments of the present invention will be described more specifically by Examples below, but the present invention is by no means restricted to the following Examples so long as it does not exceed the gist thereof.

Example 1

Synthesis of 6,8-bis{4-(pyridyl-3-yl) phenyl}-benzo[4,5]imidazo[1,2-a]pyridine (Compound-30)

In a reaction vessel were put 2,4,6-tribromoaniline: 10.0 g, 2-bromopyridine: 9.6 g, potassium carbonate: 12.6 g, copper powder: 0.2 g, and xylene: 100 mL, followed by stirring under heated reflux for 24 hours. After stirring, the mixture was allowed to stand to cool, then filtered and concentrated to obtain a crude product. Purification of the crude product was performed by using column chromatography (carrier: silica gel, eluent: dichloromethane/ethyl acetate), to thereby obtain brown powder of 6,8-dibromo-benzo[4,5]imidazo[1,2-a]pyridine: 5.9 g (yield 60%).

[Chem. 13]

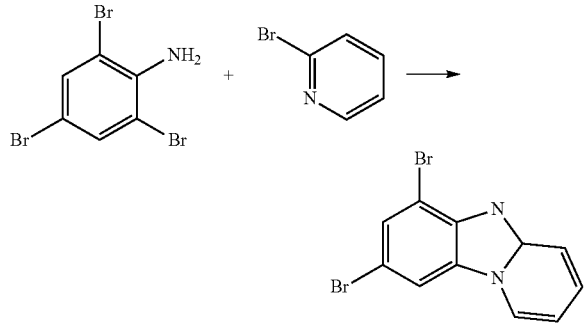

A structure of the obtained brown powder was identified with NMR.

The following 6 hydrogen signals were detected with $^1$H-NMR (DMSO-d$_6$). δ (ppm)=9.11 (1H), 8.72 (1H), 7.92 (1H), 7.77 (1H), 7.67 (1H), 7.11 (1H).

Sequentially, thereto were put 6,8-dibromo-benzo[4,5]imidazo[1,2-a]pyridine: 5.0 g, 4-(pyridyl-3-yl) phenyl boronic acid: 6.7 g, toluene: 50 mL, and ethanol: 10 mL, then an aqueous solution where potassium carbonate: 6.4 g was dissolved in H$_2$O: 20 mL in advance was further added thereto, and nitrogen gas was aerated while the solution was irradiated with ultrasonic waves for 30 minutes. To the solution where nitrogen gas was aerated was added tetrakistriphenyl phosphine palladium: 0.5 g, followed by stirring under heated reflux for 24 hours. After stirring, the solution was allowed to stand to cool, and a solid precipitated by adding methanol was collected to obtain a crude product. Purification of the crude product was performed by using column chromatography (carrier: silica gel, eluent: toluene/ethyl acetate), to thereby obtain yellow powder of 6,8-bis{4-(pyridyl-3-yl) phenyl}-benzo[4,5]imidazo[1,2-a]pyridine (Compound-30): 3.6 g (yield 50%).

[Chem. 14]

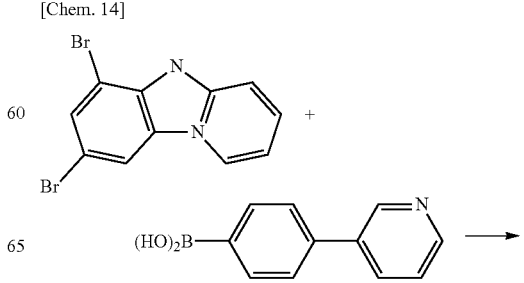

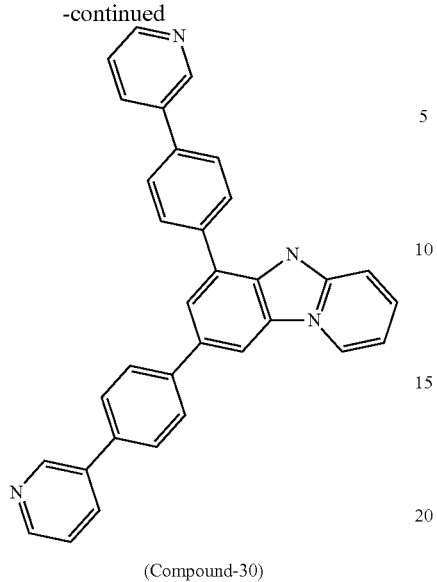

(Compound-30)

A structure of the obtained yellow powder was identified with NMR.

The following 22 hydrogen signals were detected with $^1$H-NMR (DMSO-$d_6$). δ (ppm)=9.28 (1H), 9.03 (2H), 8.82 (1H), 8.61 (2H), 8.49 (2H), 8.20 (2H), 8.19 (1H), 8.10 (2H), 7.93 (4H), 7.82 (1H), 7.64 (1H), 7.54 (2H), 7.11 (1H).

Example 2

Synthesis of 6,8-bis{4-(naphthalene-1-yl-phenyl)}-benzo[4,5]imidazo[1,2-a]pyridine (Compound-21)

In a reaction vessel were put 6,8-dibromo-benzo[4,5]imidazo[1,2-a]pyridine: 5.0 g, 4-(naphthalen-1-yl) phenyl boronic acid: 8.4 g, toluene: 50 mL, and ethanol: 10 mL, then thereto was further added an aqueous solution where potassium carbonate: 6.4 g was dissolved in H$_2$O: 20 mL in advance, and nitrogen gas was aerated while the solution was irradiated with ultrasonic waves for 30 minutes. To the solution where nitrogen gas was aerated was added tetrakistriphenyl phosphine palladium: 0.5 g, followed by stirring under heated reflux for 24 hours. After stirring, the solution was allowed to stand to cool, H$_2$O was added to perform extraction and liquid separation operation, and a collected organic layer was concentrated to obtain a crude product. Purification of the obtained crude product was performed by using column chromatography (carrier: silica gel, eluent: toluene/ethyl acetate), to thereby obtain yellow powder of 6,8-bis{4-(naphthalene-1-yl phenyl)}-benzo[4,5]imidazo[1,2-a]pyridine (Compound-21): 2.6 g (yield 30%).

[Chem. 15]

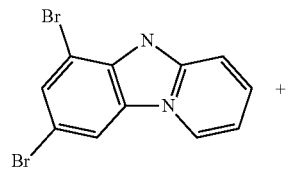

+

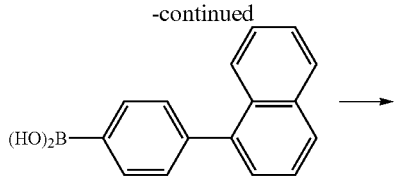

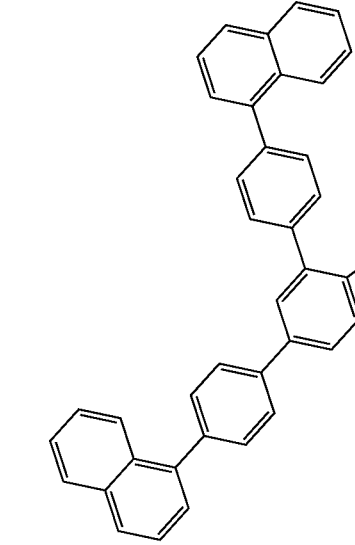

(Compound-21)

A structure of the obtained yellow powder was identified with NMR.

The following 28 hydrogen signals were detected with $^1$H-NMR (DMSO-$d_6$). δ (ppm)=9.31 (1H), 8.88 (1H), 8.52 (2H), 8.28 (1H), 8.16 (2H), 8.10 to 7.93 (6H), 7.84 (1H), 7.75 to 7.51 (13H), 7.13 (1H).

Example 3

Synthesis of 8-(9,9-diphenyl-9H-fluoren-2-yl)-6-(4-pyridin-3-yl-phenyl)-benzo[4,5]imidazo[1,2-a]pyridine (Compound-56)

In a reaction vessel were put 8-chloro-6-(4-pyridin-3-yl-phenyl)-benzo[4,5]imidazo[1,2-a]pyridine: 4.5 g, 2-(9,9-diphenyl-9H-fluorene)-boronic acid: 5.5 g, and 1,4-dioxane: 80 mL, then thereto was further added an aqueous solution where tripotassium phosphate: 8.1 g was dissolved in H$_2$O: 20 mL in advance, and nitrogen gas was aerated while the solution was irradiated with ultrasonic waves for 30 minutes. To the solution where nitrogen gas was aerated were added tris(dibenzylideneacetone) dipalladium (0): 0.3 g and tricyclohexyl phosphine: 0.4 g, followed by stirring under heated reflux for 24 hours. After stirring, the solution was allowed to stand to cool, and a solid precipitated by adding methanol was collected to obtain a crude product. Recrystallization purification of the crude product with a 1,2-dichloro benzene solvent was performed, to thereby obtain yellow powder of 8-(9,9-diphenyl-9H-fluoren-2-yl)-6-(4-pyridin-3-yl-phenyl)-benzo[4,5]imidazo[1,2-a]pyridine (Compound-56): 3.7 g (yield 46%).

[Chem. 16]

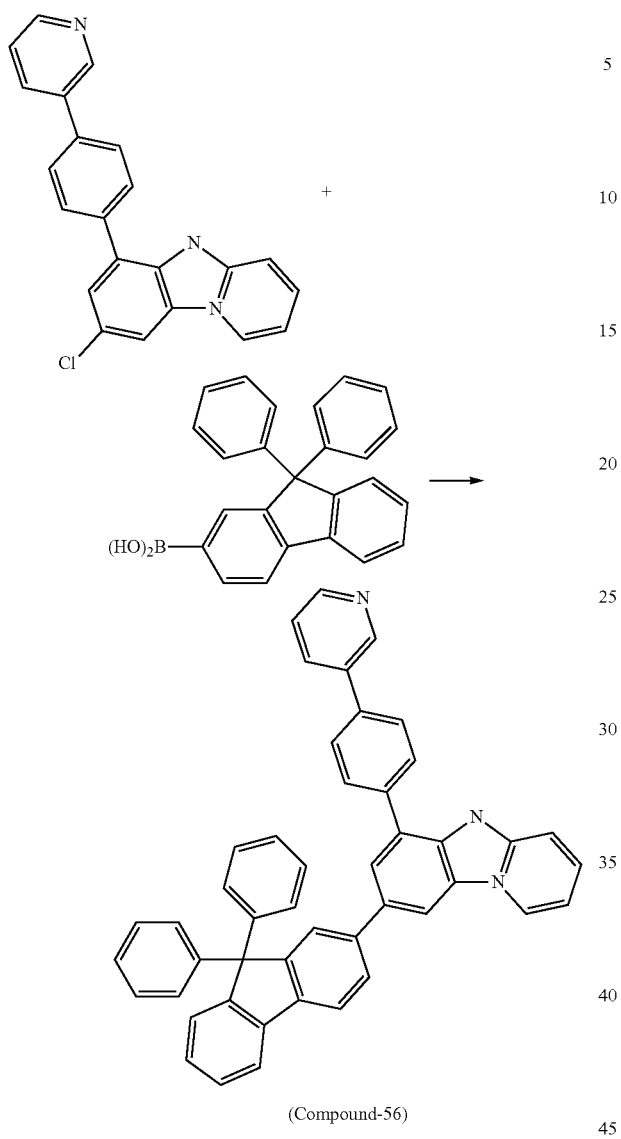

(Compound-56)

A structure of the obtained yellow powder was identified with NMR.

The following 31 hydrogen signals were detected with $^1$H-NMR (DMSO-d$_6$). δ (ppm)=9.26 (1H), 9.02 (1H), 8.69 (1H), 8.61 (1H), 8.41 (2H), 8.20 (1H), 8.11 (1H), 8.02 (4H), 7.92 (2H), 7.79 (1H), 7.62 (1H), 7.54 (1H), 7.45 (2H), 7.39 to 7.21 (11H), 7.09 (1H).

Example 4

Synthesis of 8-(9,9'-spirobi-9H-fluoren-2-yl)-6-(4-pyridyl-3-yl-phenyl)-benzo[4,5]imidazo[1,2-a]pyridine (Compound-57)

In a reaction vessel were put 8-chloro-6-(4-pyridin-3-yl-phenyl)-benzo[4,5]imidazo[1,2-a]pyridine: 3.5 g, 2-(9,9'-spirobi-9H-fluorene)-boronic acid: 4.6 g, and 1,4-dioxane: 70 mL, then thereto was further added an aqueous solution where tripotassium phosphate: 6.3 g was dissolved in H$_2$O: 15 mL in advance, and nitrogen gas was aerated while the solution was irradiated with ultrasonic waves for 30 minutes. To the solution where nitrogen gas was aerated were added tris(dibenzylideneacetone) dipalladium (0): 0.2 g and tricyclohexyl phosphine: 0.3 g, followed by stirring under heated reflux for 24 hours. After stirring, the solution was allowed to stand to cool, and a solid precipitated by adding methanol was collected to obtain a crude product. Purification of the obtained crude product was performed by using column chromatography (carrier: silica gel, eluent: toluene/ethyl acetate), to thereby obtain yellow powder of 8-(9,9'-spirobi-9H-fluoren-2-yl)-6-(4-pyridyl-3-yl-phenyl)-benzo[4,5]imidazo[1,2-a]pyridine (Compound-57): 4.3 g (yield 69%).

[Chem. 17]

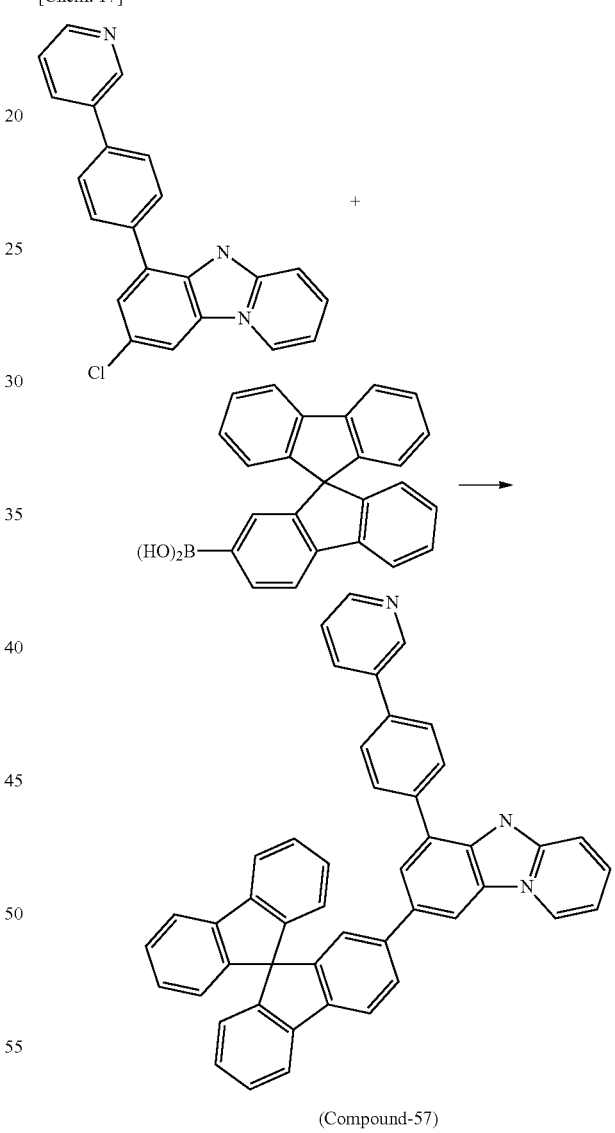

(Compound-57)

A structure of the obtained yellow powder was identified with NMR.

The following 29 hydrogen signals were detected with $^1$H-NMR (DMSO-d$_6$). δ (ppm)=9.17 (1H), 9.00 (1H), 8.60 (1H), 8.44 (1H), 8.31 (2H), 8.21 (1H), 8.17 (1H), 8.09 (1H), 8.06 (2H), 8.03 (1H), 7.88 (3H), 7.73 (1H), 7.57 (1H), 7.53 (1H), 7.43 (3H), 7.16 (4H), 6.92 (1H), 6.73 (2H), 6.57 (1H).

Example 5

Synthesis of 8-(4'-cyano-biphenyl-4-yl)-6-(4-pyridyl-3-yl-phenyl)-benzo[4,5]imidazo[1,2-a]pyridine (Compound-71)

In a reaction vessel were put 8-chloro-6-(4-pyridin-3-yl-phenyl)-benzo[4,5]imidazo[1,2-a]pyridine: 3.5 g, 4'-(4,4,5,5-tetramethyl-[1,3,2]dioxaborolan-2-yl) biphenyl-4-carbonitrile: 3.3 g, 1,4-dioxane: 60 mL, and THF: 15 mL, then thereto was further added an aqueous solution where tripotassium phosphate: 6.3 g was dissolved in H₂O: 15 mL in advance, and nitrogen gas was aerated while the solution was irradiated with ultrasonic waves for 30 minutes. To the solution where nitrogen gas was aerated were added tris(dibenzylideneacetone) dipalladium (0): 0.2 g and tricyclohexyl phosphine: 0.3 g, followed by stirring under heated reflux for 24 hours. After stirring, the solution was allowed to stand to cool, and a solid precipitated by adding methanol was collected to obtain a crude product. Purification of the obtained crude product was performed by using column chromatography (carrier: silica gel, eluent: toluene/ethyl acetate), to thereby obtain yellow powder of 8-(4'-cyano-biphenyl-4-yl)-6-(4-pyridyl-3-yl-phenyl)-benzo[4,5]imidazo[1,2-a]pyridine (Compound-71): 3.2 g (yield 65%).

[Chem. 18]

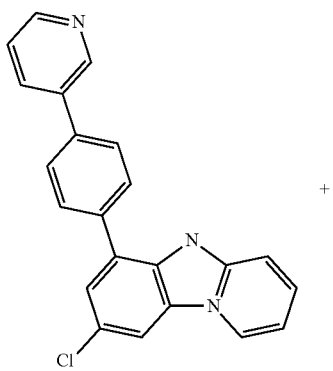

+

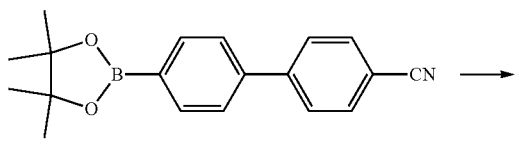

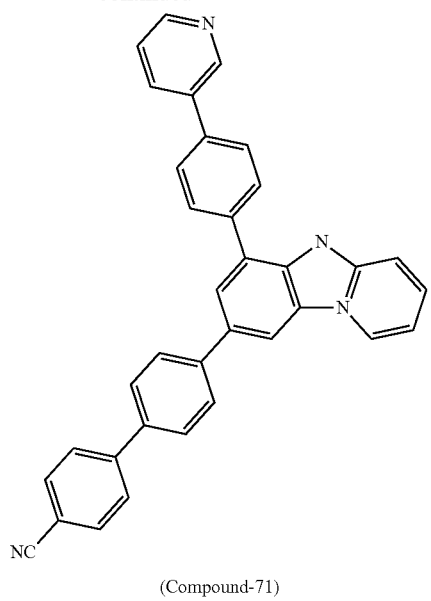

(Compound-71)

A structure of the obtained yellow powder was identified with NMR.

The following 22 hydrogen signals were detected with $^1$H-NMR (DMSO-d$_6$). δ (ppm)=9.28 (1H), 9.03 (1H), 8.83 (1H), 8.62 (1H), 8.49 (2H), 8.22 (1H), 8.19 (1H), 8.12 (2H), 8.07 to 7.90 (8H), 7.82 (1H), 7.64 (1H), 7.55 (1H), 7.12 (1H).

Example 6

A melting point and a glass transition point of the compound having a benzimidazole ring structure represented by the general formula (1) were measured with a high sensitivity differential scanning calorimeter (DSC 3100 SA, manufactured by Bruker AXS GmbH).

|  | Melting point | Glass transition point |
| --- | --- | --- |
| Compound of Example 1 | 238° C. | 112° C. |
| Compound of Example 2 | 242° C. | 130° C. |
| Compound of Example 3 | 334° C. | 164° C. |
| Compound of Example 4 | 278° C. | 177° C. |
| Compound of Example 5 | 240° C. | 126° C. |

The compound having a benzimidazole ring structure represented by the general formula (1) had a glass transition point of 100° C. or higher. This indicates that the thin film state is stable.

Example 7

The compound having a benzimidazole ring represented by the general formula (1) was used to prepare a vapor deposition film having a film thickness of 100 nm on an ITO substrate, and a work function of the film was measured with an ionization potential measuring device (PYS-202, manufactured by Sumitomo Heavy Industries, Ltd.).

|  | Work function |
| --- | --- |
| Compound of Example 1 | 6.01 eV |
| Compound of Example 2 | 5.97 eV |
| Compound of Example 3 | 5.95 eV |
| Compound of Example 4 | 5.95 eV |
| Compound of Example 5 | 6.00 eV |

The compound having a benzimidazole ring represented by the general formula (1) exhibited a suitable energy level as compared with a work function of 5.8 eV to 6.0 eV of a general electron transport material such as $Alq_3$. From this, it can be found that the compounds have good electron transport ability.

Example 8

As illustrated in FIG. 1, an organic EL device of this Example was prepared by depositing a hole injection layer 3, a hole transport layer 4, a light emitting layer 5, a hole blocking layer and electron transport layer 6, an electron injection layer 7, and a cathode (aluminum electrode) 8 in this order on a glass substrate 1 on which an ITO electrode had been formed as a transparent anode 2 in advance.

Specifically, an organic EL device was prepared by the following procedure. The glass substrate 1 on which ITO having a film thickness of 50 nm was formed was subjected to ultrasonic washing in isopropyl alcohol for 20 minutes, and then dried for 10 minutes on a hot plate heated to 200° C. Then, after performing a UV ozone treatment for 15 minutes, the glass substrate with ITO was mounted in a vacuum deposition machine and depressurized to 0.001 Pa or less. Subsequently, an electron acceptor (Acceptor-1) of the following structural formula and a compound (HTM-1) of the following structural formula were subjected to binary deposition on the transparent anode 2 at a deposition rate such that a deposition rate ratio of Acceptor-1:HTM-1=3:97. Thus, the hole injection layer 3 covering the transparent anode 2 was formed to have a film thickness of 10 nm. The compound (HTM-1) of the following structural formula was deposited on the hole injection layer 3, to form the hole transport layer 4 so as to have a film thickness of 60 nm. A compound (EMD-1) of the following structural formula and a compound (EMH-1) of the following structural formula were subjected to binary deposition on the hole transport layer 4 at a deposition rate such that a deposition rate ratio of EMD-1:EMH-1=5:95. As a result, the light emitting layer 5 was formed to have a film thickness of 20 nm. A compound (Compound-30) of Example 1 and a compound (ETM-1) of the following structural formula were subjected to binary deposition on the light emitting layer 5 at a deposition rate such that a deposition rate ratio of Compound-30:ETM-1=50:50. As a result, the hole blocking layer and electron transport layer 6 was formed to have a film thickness of 30 nm. Lithium fluoride was deposited on the hole blocking layer and electron transport layer 6, to form the electron injection layer 7 so as to have a film thickness of 1 nm. Finally, aluminum was deposited thereon to form the cathode 8 so as to have a film thickness of 100 nm. The produced organic EL device was subjected to characteristic measurement in the atmosphere at room temperature. Table 1 summarized measurement results of light emitting characteristics when a direct current voltage was applied to the produced organic EL device.

[Chem. 19]

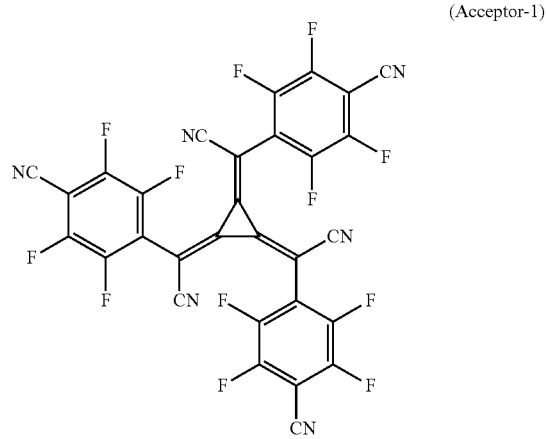

(Acceptor-1)

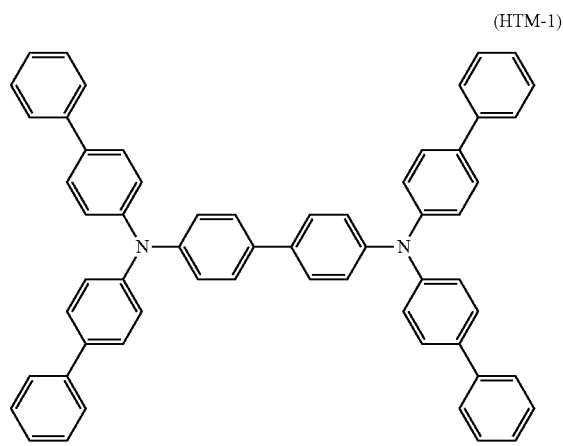

(HTM-1)

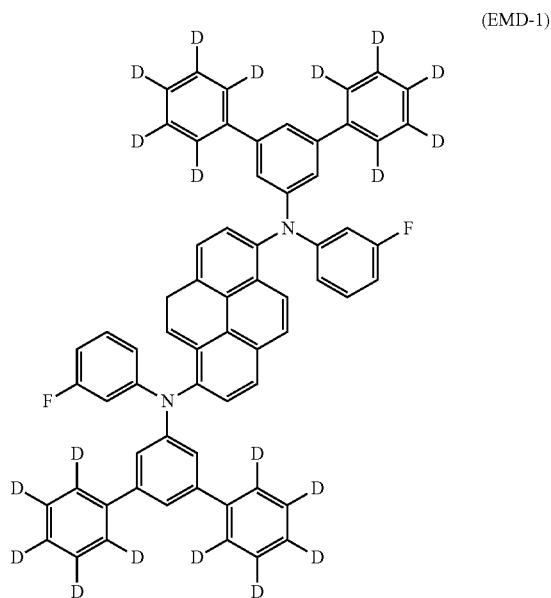

(EMD-1)

-continued

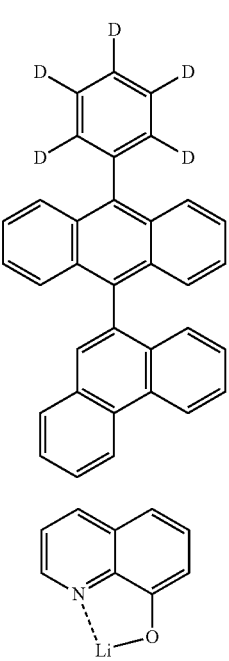

(EMH-1)

(ETM-1)

Example 9

An organic EL device was produced under the same conditions as in Example 8, except that the compound (Compound-21) of Example 2 was used instead of the compound (Compound-30) of Example 1 as a material of the hole blocking layer and electron transport layer 6 and a binary deposition was performed at a deposition rate such that a deposition rate ratio of Compound-21:ETM-1=50:50. The produced organic EL device was subjected to characteristic measurement in the atmosphere at room temperature. Table 1 summarized measurement results of light emitting characteristics when a direct current voltage was applied to the produced organic EL device.

Example 10

An organic EL device was produced under the same conditions as in Example 8, except that the compound (Compound-56) of Example 3 was used instead of the compound (Compound-30) of Example 1 as a material of the hole blocking layer and electron transport layer 6 and a binary deposition was performed at a deposition rate such that a deposition rate ratio of Compound-56:ETM-1=50:50. The produced organic EL device was subjected to characteristic measurement in the atmosphere at room temperature. Table 1 summarized measurement results of light emitting characteristics when a direct current voltage was applied to the produced organic EL device.

Example 11

An organic EL device was produced under the same conditions as in Example 8, except that the compound (Compound-57) of Example 4 was used instead of the compound (Compound-30) of Example 1 as a material of the hole blocking layer and electron transport layer 6 and a binary deposition was performed at a deposition rate such that a deposition rate ratio of Compound-57:ETM-1=50:50. The produced organic EL device was subjected to characteristic measurement in the atmosphere at room temperature. Table 1 summarized measurement results of light emitting characteristics when a direct current voltage was applied to the produced organic EL device.

Example 12

An organic EL device was produced under the same conditions as in Example 8, except that the compound (Compound-71) of Example 5 was used instead of the compound (Compound-30) of Example 1 as a material of the hole blocking layer and electron transport layer 6 and a binary deposition was performed at a deposition rate such that a deposition rate ratio of Compound-71:ETM-1=50:50. The produced organic EL device was subjected to characteristic measurement in the atmosphere at room temperature. Table 1 summarized measurement results of light emitting characteristics when a direct current voltage was applied to the produced organic EL device.

Comparative Example 1

For comparison, an organic EL device was produced under the same conditions as in Example 8, except that the compound (ETM-2) (see, e.g., Patent Literature 6) of the following structural formula was used instead of the compound (Compound-30) of Example 1 as a material of the hole blocking layer and electron transport layer 6 and a binary deposition was performed at a deposition rate such that a deposition rate ratio of ETM-2:ETM-1=50:50. The produced organic EL device was subjected to characteristic measurement in the atmosphere at room temperature. Table 1 summarized measurement results of light emitting characteristics when a direct current voltage was applied to the produced organic EL device.

[Chem. 20]

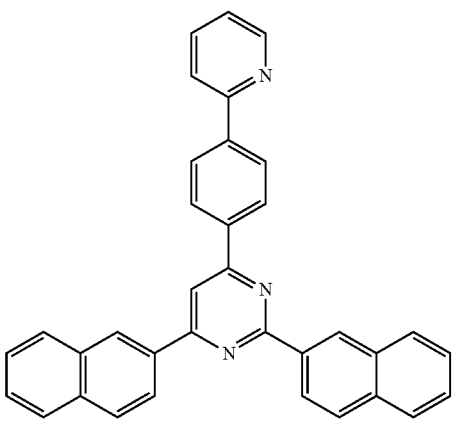

(ETM-2)

Comparative Example 2

For comparison, an organic EL device was produced under the same conditions as in Example 8, except that a compound (ETM-3) (see, e.g., Patent Literature 7) of the following structural formula was used instead of the compound (Compound-30) of Example 1 as a material of the hole blocking layer and electron transport layer 6 and a binary deposition was performed at a deposition rate such that a deposition rate ratio of ETM-3:ETM-1=50:50. The produced organic EL device was subjected to characteristic measurement in the atmosphere at room temperature. Table 1 summarized measurement results of light emitting characteristics when a direct current voltage was applied to the produced organic EL device.

produced organic EL device was subjected to characteristic measurement in the atmosphere at room temperature. Table 1 summarized measurement results of light emitting characteristics when a direct current voltage was applied to the produced organic EL device.

[Chem. 21]

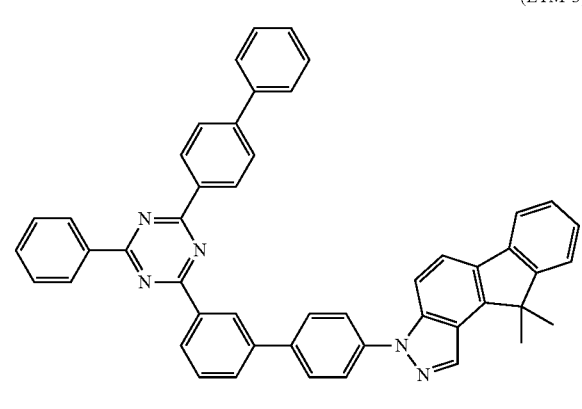

(ETM-3)

[Chem. 22]

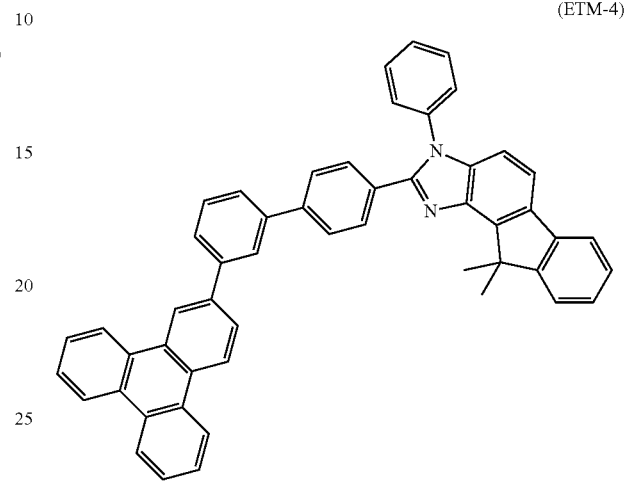

(ETM-4)

Comparative Example 3

For comparison, an organic EL device was produced under the same conditions as in Example 8, except that a compound (ETM-4) (see, e.g., Patent Literature 7) of the following structural formula was used instead of the compound (Compound-30) of Example 1 as a material of the hole blocking layer and electron transport layer 6 and a binary deposition was performed at a deposition rate such that a deposition rate ratio of ETM-4:ETM-1=50:50. The Table 1 summarized results of measuring a device lifetime by using the organic EL devices produced in Examples 8 to 12 and Comparative Examples 1 to 3. The device lifetime was measured as time until the emission luminance attenuated to 1,900 cd/m$^2$ when a constant-current driving was performed at an emission luminance (initial luminance) of 2,000 cd/m$^2$ at the light-emission start (equivalent to 95% of the initial luminance which is regarded as 100%: 95% attenuation).

TABLE 1

|  | Hole blocking layer and electron transport layer | Voltage [V] (@ 10 mA/cm$^2$) | Luminance [cd/m$^2$] (@ 10 mA/cm$^2$) | Luminous efficiency [cd/A] (@ 10 mA/cm$^2$) | Power efficiency [lm/W] (@ 10 mA/cm$^2$) | Device lifetime 95% attenuation |
| --- | --- | --- | --- | --- | --- | --- |
| Example 8 | Compound-30/ ETM-1 | 3.43 | 896 | 8.96 | 8.22 | 138 hours |
| Example 9 | Compound-21/ ETM-1 | 3.39 | 897 | 8.97 | 8.32 | 134 hours |
| Example 10 | Compound-56/ ETM-1 | 3.49 | 871 | 8.72 | 7.85 | 146 hours |
| Example 11 | Compound-57/ ETM-1 | 3.51 | 865 | 8.66 | 7.75 | 158 hours |
| Example 12 | Compound-71/ ETM-1 | 3.53 | 861 | 8.62 | 7.68 | 178 hours |
| Comparative Example 1 | ETM-2/ ETM-1 | 3.66 | 753 | 7.53 | 6.45 | 43 hours |
| Comparative Example 2 | ETM-3/ ETM-1 | 3.76 | 695 | 6.95 | 5.80 | 65 hours |
| Comparative Example 3 | ETM-4/ ETM-1 | 3.81 | 762 | 7.62 | 6.28 | 63 hours |

As shown in Table 1, a drive voltage when a current having a current density of 10 mA/cm² flows was 3.66 V to 3.81 V in the organic EL devices of Comparative Examples 1 to 3 using the compounds ETM-2 to ETM-4 of the above-mentioned structural formulae. In contrast, in the organic EL devices of Examples 8 to 12, the drive voltage was 3.39 V to 3.53 V, and reduction in voltage was confirmed.

Luminous efficiency of the organic EL devices of Comparative Examples 1 to 3 was 6.95 cd/A to 7.62 cd/A. In contrast, in the organic EL devices of Examples 8 to 12, the luminous efficiency was 8.62 cd/A to 8.97 cd/A, and improvement in luminous efficiency was confirmed.

Power efficiency of the organic EL devices of Comparative Examples 1 to 3 was 5.80 lm/W to 6.45 lm/W. In contrast, in the organic EL devices of Examples 8 to 12, the power efficiency was 7.68 lm/W to 8.32 lm/W, and improvement in power efficiency was confirmed.

A device lifetime (95% attenuation) of the organic EL devices of Comparative Examples 1 to 3 was 43 to 65 hours. In contrast, in the organic EL devices of Examples 8 to 12, the device lifetime was 134 to 178 hours, and particularly long lifetime was confirmed.

In this way, it has been found that the organic EL device of the present invention has excellent luminous efficiency and power efficiency and an organic EL device having a long lifetime can be realized, as compared with a device using the compounds (ETM-2 to ETM-4) of the structural formulae shown in Comparative Examples.

Although the present invention has been described in detail and by reference to specific embodiments, it is apparent to those skilled in the art that it is possible to add various changes and modifications without departing from the spirit and the scope of the present invention.

The present application is based on Japanese Patent Application (No. 2018-55656) filed on Mar. 23, 2018, the entirety of which is incorporated by reference. All references cited herein are entirely incorporated.

INDUSTRIAL APPLICABILITY

The compound having a specific benzimidazole ring of the present invention has good electron injection characteristics and excellent electron transport ability, and is stable in a thin film state, and thus is excellent as a compound for an organic EL device. When an organic EL device is produced by using the compound, high efficiency can be obtained, a drive voltage can be reduced, and durability can be improved. For example, it is possible to develop a home electrical appliance or a lighting application.

REFERENCE SIGNS LIST

1 Glass substrate
2 Transparent anode
3 Hole injection layer
4 Hole transport layer
5 Light emitting layer
6 Hole blocking layer and electron transport layer
7 Electron injection layer
8 Cathode

The invention claimed is:
1. A compound having a benzimidazole ring structure, represented by the following general formula (1):

[Chem. 23]

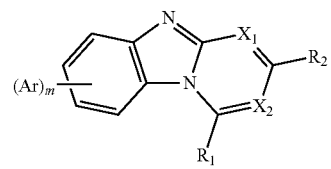

(1)

(in the formula, $X_1$ and $X_2$ may be the same as or different from each other, and each represent a carbon atom having a hydrogen atom, a deuterium atom, a fluorine atom, a chlorine atom, a cyano group, a nitro group, a trimethylsilyl group, or a triphenylsilyl group, a carbon atom having a substituted or unsubstituted aromatic hydrocarbon group, a carbon atom having a substituted or unsubstituted aromatic heterocyclic group, a carbon atom having a substituted or unsubstituted condensed polycyclic aromatic group, a carbon atom having a linear or branched alkyl group having a carbon number of 1 to 6 which may have a substituent, a carbon atom having a cycloalkyl group having a carbon number of 5 to 10 which may have a substituent, a carbon atom having a linear or branched alkenyl group having a carbon number of 2 to 6 which may have a substituent, a carbon atom having a linear or branched alkyloxy group having a carbon number of 1 to 6 which may have a substituent, a carbon atom having a cycloalkyloxy group having a carbon number of 5 to 10 which may have a substituent, or a nitrogen atom;

Ar represents a substituted or unsubstituted aromatic hydrocarbon group, a substituted or unsubstituted aromatic heterocyclic group, or a substituted or unsubstituted condensed polycyclic aromatic group;

$R_1$ and $R_2$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m is an integer of 2, wherein a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring) and with the proviso that at least one Ar group cannot be an unsubstituted phenyl group.

2. The compound having a benzimidazole ring structure according to claim 1, represented by the following general formula (2):

[Chem. 24]

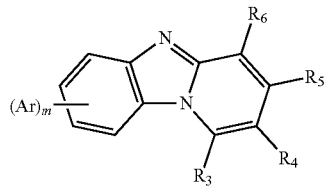

(2)

(in the formula, Ar represents a substituted or unsubstituted aromatic hydrocarbon group, a substituted or unsubstituted aromatic heterocyclic group, or a substituted or unsubstituted condensed polycyclic aromatic group;

$R_3$ to $R_6$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m is an integer of 2, wherein a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring).

3. The compound having a benzimidazole ring structure according to claim 1, represented by the following general formula (3):

[Chem. 25]

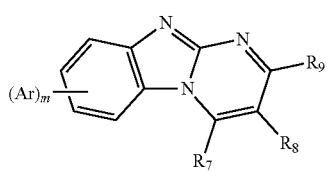

(3)

(in the formula, Ar represents a substituted or unsubstituted aromatic hydrocarbon group, a substituted or unsubstituted aromatic heterocyclic group, or a substituted or unsubstituted condensed polycyclic aromatic group;

$R_7$ to $R_9$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent; and m is an integer of 2, wherein a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring).

4. A compound having a benzimidazole ring structure, represented by the following general formula (4):

[Chem. 5]

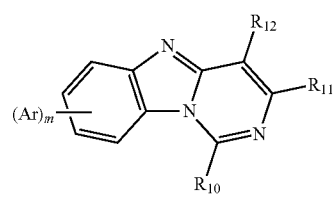

(4)

(in the formula, Ar represents a substituted or unsubstituted aromatic hydrocarbon group, a substituted or unsubstituted aromatic heterocyclic group, or a substituted or unsubstituted condensed polycyclic aromatic group;

$R_{10}$ to $R_{12}$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent;

m represents an integer of 0 to 4; and in a case where m is an integer of 2 or more, a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring).

5. A compound having a benzimidazole ring structure, represented by the following general formula (5):

[Chem. 27]

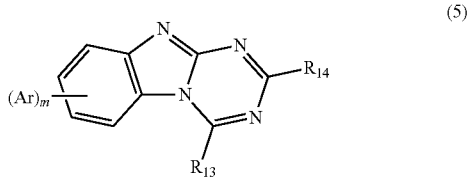

(5)

(in the formula, Ar represents a substituted or unsubstituted aromatic hydrocarbon group, a substituted or unsubstituted aromatic heterocyclic group, or a substituted or unsubstituted condensed polycyclic aromatic group;

$R_{13}$ and $R_{14}$ may be the same as or different from each other, and each represent a hydrogen atom, a deuterium atom, a fluorine atom, a chlorine atom, a cyano group, a nitro group, a trimethylsilyl group, a triphenylsilyl group, a substituted or unsubstituted aromatic hydrocarbon group, a substituted or unsubstituted aromatic heterocyclic group, a substituted or unsubstituted condensed polycyclic aromatic group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, or a cycloalkyloxy group having a carbon number of 5 to 10 which may have a substituent;

m represents an integer of 0 to 4; and in a case where m is an integer of 2 or more, a plurality of Ar's bonded to the same benzene rings may be the same as or different from each other, and may be bonded to each other via a single bond, a substituted or unsubstituted methylene group, a substituted or unsubstituted amino group, an oxygen atom, or a sulfur atom, to form a ring along with the substituted benzene ring).

6. An organic electroluminescence device comprising a pair of electrodes and at least one organic layer sandwiched therebetween, wherein the at least one organic layer comprises the compound having a benzimidazole ring structure as described in claim 1.

7. The organic electroluminescence device according to claim 6, wherein the organic layer containing the compound having a benzimidazole ring structure is an electron transport layer.

8. The organic electroluminescence device according to claim 6, wherein the organic layer containing the compound having a benzimidazole ring structure is a hole blocking layer.

9. The organic electroluminescence device according to claim 6, wherein the organic layer containing the compound having a benzimidazole ring structure is a light emitting layer.

10. The organic electroluminescence device according to claim 6, wherein the organic layer containing the compound having a benzimidazole ring structure is an electron injection layer.

* * * * *